US010993879B2

(12) United States Patent
Lee et al.

(10) Patent No.: US 10,993,879 B2
(45) Date of Patent: May 4, 2021

(54) PULMONARY DELIVERY OF PROGESTOGEN

(71) Applicant: SHENZHEN EVERGREEN THERAPEUTICS CO., LTD., Shenzhen (CN)

(72) Inventors: Chang Lee, Bethesda, MD (US); Tao Tom Du, North Potomac, MD (US)

(73) Assignee: SHENZHEN EVERGREEN THERAPEUTICS CO., LTD., Shenzhen (CN)

( * ) Notice: Subject to any disclaimer, the term of this patent is extended or adjusted under 35 U.S.C. 154(b) by 0 days.

(21) Appl. No.: 14/860,578

(22) Filed: Sep. 21, 2015

(65) Prior Publication Data

US 2016/0045396 A1 Feb. 18, 2016

Related U.S. Application Data

(63) Continuation-in-part of application No. 13/174,939, filed on Jul. 1, 2011, now abandoned, which is a continuation-in-part of application No. 13/021,950, filed on Feb. 7, 2011, now Pat. No. 10,231,976.

(60) Provisional application No. 62/195,649, filed on Jul. 22, 2015, provisional application No. 61/302,325, filed on Feb. 8, 2010.

(51) Int. Cl.

| | |
|---|---|
| *A61J 3/02* | (2006.01) |
| *A61K 9/36* | (2006.01) |
| *A61K 9/00* | (2006.01) |
| *A61K 31/573* | (2006.01) |
| *A61K 31/58* | (2006.01) |
| *A61K 31/56* | (2006.01) |
| *A61K 31/57* | (2006.01) |

(52) U.S. Cl.

CPC ............... *A61J 3/02* (2013.01); *A61K 9/0075* (2013.01); *A61K 31/56* (2013.01); *A61K 31/57* (2013.01); *A61K 31/573* (2013.01); *A61K 31/58* (2013.01); *A61K 9/0019* (2013.01)

(58) Field of Classification Search

CPC ........................................................ A61J 3/02

See application file for complete search history.

(56) References Cited

U.S. PATENT DOCUMENTS

| | | | | |
|---|---|---|---|---|
| 2001/0033870 | A1 | 10/2001 | Luo et al. | |
| 2002/0173669 | A1 | 11/2002 | Schultz et al. | |
| 2004/0162274 | A1 | 8/2004 | Paust et al. | |
| 2004/0234610 | A1 | 11/2004 | Hall et al. | |
| 2005/0042268 | A1 | 2/2005 | Aschkenasy et al. | |
| 2006/0052306 | A1* | 3/2006 | Costantino | A61K 9/0043 514/11.8 |
| 2006/0182691 | A1 | 8/2006 | Besse et al. | |
| 2006/0275360 | A1 | 12/2006 | Ahmed et al. | |
| 2007/0020197 | A1 | 1/2007 | Galli et al. | |
| 2007/0178166 | A1* | 8/2007 | Bernstein | A61K 9/0043 424/499 |
| 2008/0269178 | A1* | 10/2008 | Miller | A61K 9/0073 514/177 |
| 2009/0035375 | A1 | 2/2009 | Skrtic et al. | |
| 2009/0221544 | A1* | 9/2009 | Stein | A61K 31/57 514/177 |
| 2010/0316724 | A1 | 12/2010 | Whitfield et al. | |
| 2011/0195031 | A1* | 8/2011 | Du | A61K 31/56 424/43 |
| 2011/0262502 | A1* | 10/2011 | Lee | A61K 9/0075 424/400 |
| 2013/0029957 | A1 | 1/2013 | Giliyar et al. | |
| 2013/0203717 | A1 | 8/2013 | Gil | |
| 2013/0303502 | A1 | 11/2013 | Cavanagh et al. | |
| 2016/0045517 | A1 | 2/2016 | Du et al. | |

FOREIGN PATENT DOCUMENTS

| | | | |
|---|---|---|---|
| EP | 2050437 | * | 10/2007 |
| WO | WO-2006/138518 | A1 | 12/2006 |
| WO | PCT/US11/23917 | | 12/2011 |

OTHER PUBLICATIONS

Keck et al. Drug Nanocrystals of Poorly Soluble Drugs Produced by High Pressure Homogenization. 2006.*
Araya-Sibaja, Andrea Mariela et al. "Dissolution properties, solid state transformation and polymorphic crystallization: progesterone case study." Pharmceutical Development and Technology. Nov. 2014;19(7):779-88.
Junyaprasert, Varaporn B. et al. "Nanocrystals for enhancement of oral bioavailability of poorly water soluble drugs." Asian Journal of Pharmaceutical Sciences. (10)1:13-23. 2015.
Larran, Jean M. "Micronisation of pharmaceutical powders for use in inhalation." Pharmaceutical Manufacturing and Packaging Sourcer. Spring 2005.
Lonare, Abhijit A. et al. "Antisolvent crystallization of poorly water soluble drugs." International Journal of Chemical Engineering and Applications. vol. 4(5): 337-341. 2013.

Nekkanti, Vijaykumar et al. "Drug Nanoparticles—An Overview". The Delivery of Nanoparticles. 2012. ISBN:978:953-51-0615-9.

Junghanns, Jens-Uwe A.H. et al. "Nanocrystal Technology, Drug Delivery and Clinical Applications." International Journal of Nanomedicine. Sep; 3(3): 295-310. 2008.

(Continued)

*Primary Examiner* — Sarah Alawadi

(74) *Attorney, Agent, or Firm* — Foley & Lardner LLP

(57) ABSTRACT

The present invention relates to a pharmaceutical formulation powder that contains 17α-hydroxyprogesterone caproate (17-OHPC) powder and the method of producing the formulation produces particles that are suitable as an inhalant. The formulations, methods and kits of powdered 17-OHPC as taught herein may be used to reduce cytokine interleukin-17 (IL-17 or IL-17A) levels in both broncheoalveolar lavage fluid (BALF) and blood/serum and involve the inhibition of p38 mitogen activating protein kinase (MAPK) activity. The 17-OHPC powder formulation may be used in a method to treat IL-17 cytokine and/or p38 MAPK mediated auto-immune and auto-inflammatory diseases. Such diseases may include glucocorticoid (GC) insensitive related diseases or conditions. In alternate embodiment, the formulation may include the combined use of budesonide (BUD) and/or fluticasone with 17-OPHC.

8 Claims, 11 Drawing Sheets

(56) References Cited

OTHER PUBLICATIONS

Sani, Shabnam N. et al. "Effect of microfluidization parameters on the physical properties of PEG-PLGA nanoparticles prepared using high pressure microfluidization." Journal of Microencapsulation. Sep;26(6):556-561. 2009.

Nakach, Mostafa et al. "Comparison of various milling technologies for grinding pharmaceuticals." International Journal of Mineral Processing. 74:S173-181. Dec. 2004.

Konya, Christine et al."Update on the role of Interleukin 17 in rheumatologic autoimmune diseases." Cytokine. Oct. 2015:75(2):207-15.

Keck, Cornelia M. et al. "Drug Nanocrystals of poorly soluble drugs produces by high pressure homogenization." European Journal of Pharmaceuticals and Biopharmaceutics. Jan;62(1):3-16. 2006.

Möschwitzer, Jan P. "Drug Nanocrystals in the commercial pharmaceutical development process." International Journal or Pharmaceutics. 453:142-156. 2013.

Shegokar, Ranjita et al. "Nanocrystals: Industrially feasible multifunctional formulation technology for poorly soluble actives." International Journal of Pharmaceutics. Oct. 31;399(1-2):129-39. 2010.

Krause, K.P. et al. "Heavy metal contamination of nanosuspension produced by high pressure homogenisation." International Journal of Pharmaceutics. Mar. 10;196(2):169-72. 2000.

Labiris, N.R. et al. "Pulmonary drug delivery. Part I: Physiological factors affecting therapeutic effectiveness of aerosolized medications." British Journal Clinical Pharmacology. Dec; 56(6): 588-599. 2003.

Suzuki, Hidemi et al. "Role of Complement Activation in Obliterative Bronchiolitis Post-Lung Transplantation." The Journal of Immunology. 2013; 191:4431-4439.

Djupesland, Per G. "Nasal drug delivery devices: characteristics and performance in a clinical perspective—a review." Drug Delivery and Translational Research. Feb;3(1):42-62. 2013.

Busse, William W., et al. "Randomized, Double-Blind, Placebo-controlled Study of Brodalumab, a Human Anti-IL-17 Receptor Monoclonal Antibody, in Moderate to Severe Asthma." American Journal Respiratory and Critical Care Medicine vol. 188, Iss. 11, pp. 1294-1302, Dec. 1, 2013.

Amara, Suneetha et al. "Synergistic effect of pro-inflammatory TNF and IL-17 in periostin mediated collagen deposition: Potential role in liver fibrosis." Molecular Immunology 64.1 (2015): 26-35.

Siew, Adeline. "Pulmonary Drug delivery—Particle Engineering for Inhaled Therapeutics." Pharmaceutical Technology. Feb. 2014(38);2. 2014.

Khadka, Prakash et al. "Pharmaceutical particle technologies: An approach to improve drug solubility, dissolution and bioavailability." Asian Journal of Pharmaceutical Sciences. Dec(9)6:304-316. 2014.

Dvorsky, Richard et al. "Dynamics analysis of cavitation disintegration of microparticles during nanopowder preparation in a new water jet mill (wjm) device." Advanced Powder Technology. 22:639-643. 2011.

Kim, Yang-Gyun et al. "Gene Polymorphisms of Interleukin-17 and Interleukin-17 Receptor Are Associated with End-Stage Kidney Disease." American Journal of Nephrology. 2012;36:472-477. Nov. 7, 2012.

Emamauille, Juliet A., et al. "Inhibition of Th17 Cells Regulates Autoimmune Diabetes in NOD Mice." Diabetes. vol. 58. Jun. 2009.

Knier, Benjamin et al. "Neutralizing IL-17 protects the optic nerve from autoimmune pathology and prevents retinal nerve fiber layer atrophy during experimental autoimmune encephalomyelitis." Journal of Autoimmunity. 56:34-44. Oct. 1, 2014.

Keck, Cornelia et al. "Second generation of drug Nanocrystals for delivery of poorly soluble drugs: smart crystals technology." Dosis. 24(2)124-128. 2008.

Chikhalia, V. et al., "The effect of crystal morphology and mill type on milling induced crystal disorder." European Journal of Pharmaceutical Sciences. Jan;27(1):19-26. 2006.

Bauer, John F. "Pharmaceutical Solids —The Amorphous State." Journal of Validation Technology; Aug. 2009, vol. 15 Issue 3, p. 63-68.

Gil, M. et al. "Scale-up methodology for pharmaceutical spray drying." Chemistry Today 2010. 28(4)18-22.

Srivalli, Kale M.R. et al. "Drug Nanocrystals: A way toward scale-up." Saudi Pharmaceutical Journal, May 2014.

Stirling, R.G., et al. "Severe asthma: definition and mechanism." Allergy 2001:56:825-840.

Sharma, Padmini H., et al. "Poorly Soluble Drugs—A Challenge in Drug Delivery System." European Journal of Pharmaceutical and Medical Research. 2015, 2(2), 484-502.

Kudo, Makoto. et al. "IL-17 A produced by AB T cells drives airway hyper-responsiveness in mice and enhances mouse and human airway smooth muscle contraction." Nature Medicine 2012, 4;18(4):547-54.

Bhavsar, P. et al. "Relative corticosteroid insensitivity of alveolar macrophages in severe asthma compared with non-severe asthma." Thorax. Sep. 2008;63(9):784-90.

Martinu, T., et al. "IL-17 Mediates Post-Transplant Airway and Parenchymal Lung Fibrosis." The Journal of Heart and Lung Transplantation. 463; 34:4, Apr. 2015.

Gong, Fangchen et al. "The paradoxical role of IL-17 in atherosclerosis." Cellular Immunology. May 29, 2015.

Fujino, S., et al. "Increased expression of interleukin 17 in inflammatory bowel disease." Gut; 52:65-70. 2003.

Hueber, Wolfgang et al. "Effects of AIN457, a fully human antibody interleukin-17A, on psoriasis, rheumatoid arthritis, and uveititis" Science Translational Medicine. Oct. 6, 2010;2(52):52ra72.

Gold, Ralf et al. "Interleukin-17—Extended Features of a Key Player in Multiple Sclerosis." The American Journal of Pathology. 172:1, Jan. 2008.

De Pasquale, L. et al. "Increased muscle expression of interleukin-17 in Duchenne muscular dystrophy." Neurology. 2012; 78:1309-1314.

Potvin, Stephane et al. "Inflammatory Cytokine Alterations in Schizophrenia: A Systematic Quantitative Review." Society of Biological Psychiatry. 2008;63:801-808.

Roy, Tapash et al. "Epidemiology of depression and diabetes: A systematic review." Journal of Affective Disorders. 142S1 (2012) S8-S21.

Barnes, Peter J., et al. "Mechanisms and resistance in glucocorticoid control of inflammation." Journal of Steroid Biochemistry and Molecular Biology. 120 (2010) 76-85.

François, Antoine et al., "B cell activating factor is central to bleomycin- and IL-17-mediated experimental pulmonary fibrosis." Journal of Autoimmuity. 2015, 56: 1-11.

Vehring, Reinhard. "Pharmaceutical Particle Engineering via Spray Drying." Pharmaceutical Research. May 2008; 25(5): 999-1022.

Caramori, Gaetano et al. "Cytokine inhibition in the treatment of COPD." International Journal of COPD. 2014, 9:397-412.

Cornelius, Denise C. et al. "A role for TH17 cells and IL-17 in mediating the pathophysiology associated with preeclampsia." Pregnancy Hypertension. 2015, 5 (1): 17.

Chew, Nora Y.K. et al. "Effect of Powder Polydispersity on Aerosol Generation". Journal of Pharmacy and Pharmaceutical Sciences. 5(2):162-168. 2002.

Masterisizer 2000 User Manual. MANO384 Issue 1.0 Mar. 2007. Malvern Instruments Ltd.

Qiao, Guilin et al., "A77 1726, the active metabolite of leflunomide, attenuates lupus nephritis by promoting the development of regulatory T cells and inhibiting IL-17-producing double negative T cells." Clinical Immunology. 2015, 157(2): 166-174.

Office Action issued in related U.S. Appl. No. 13/021,950 dated Aug. 12, 2016 (26 pages).

Eugynon 30 review [downloaded from the website <https://web.archive.org/web/20080421032737/http://www.ciao.co.uk/Eugynon_30_Review_5404407> on Aug. 1, 2016].

Patient Group Direction for Microgynon 30 [downloaded from the website <http://www.nes.scot.nhs.uk/media/422760/pgd_microgynon_30_dec_06.pdf> on Aug. 1, 2016].

Office Action dated Feb. 7, 2017, issued by the U.S. Patent and Trademark Office in related U.S. Appl. No. 13/021,950 (25 pages).

(56) References Cited

OTHER PUBLICATIONS

Allen, J. et al. (2015) "IL-17 and neutrophils: unexpected players in the type 2 immune response," Current Opinion in Immunology 34:99-106.
Attardi, B.J. et al. (2007) "Comparison of progesterone and glucocorticoid receptor binding and stimulation of gene expression by progesterone, 17-alpha hydroxyprogesterone caproate, and related progestins," Amer J Obstetrics Gyn 197:599.e.1.
Aujla, S.J. et al. (2008) "IL-22 mediates mucosal host defense against Gram-negative bacterial pneumonia," Nature Medicine 14(3):275-281.
Beynon, H.L. et al. (1988) "Severe premenstrual exacerbations of asthma: effect of intramuscular progesterone," Lancet 2(8607):37p0-372.
Boardman, C. et al. (2014) "Mechanisms of glucocorticoid action and insensitivity in airways disease," Pulmonary Pharmacology & Therapeutics 29(2):129-143.
Caritis, S.N. et al. (2011) "Pharmacokinetics of 17-hydroxyprogesterone caproate in multifetal gestation," Am J Obstet Gynecol. 205(1):40.e1-40.e8.
Chrousos, G.P. (2014) "Hyperaldosteronism Differential Diagnoses," Hyperaldosteronism Differential Diagnoses. Medscape, Web.
Chung, K.F. et al. (2011) "p38 Mitogen-Activated Protein Kinase Pathways in Asthma and COPD," CHEST 139(6):1470-1479.
Coulthard, L.R. et al. (2009) "p38MAPK: stress responses from molecular mechanisms to therapeutics," Trends Mol Med. 15(8):369-379.
Creed, T.J. et al. (2009) "The Effects of Cytokines on Suppression of Lymphocyte Proliferation by Dexamethasone," J Immunol 183:164-171.
Dalton, K. (1976) "Progesterone or progestogens?" Br Med J 2:1257.
Dvorsky, R. et al. (2011) "Dynamics analysis of cavitation disintegration of microparticles during nanopowder preparation in a new Water Jet Mill (WJM) device," Advanced Powder Technology 22:639-643.
Ettmeyer, P. et al. (2004) "Lessons Learned from Marketed and Investigational Prodrugs," J. Medicinal Chem. 47(10):2393-2404.
Falchetti, R. et al. (1998) "Determination of cytokine co-expression in individual splenic CD4 and CD8 T cells from influenze virus-immune mice," Immunology 95:346-351.
Final Office Action in U.S. Appl. No. 13/021,950, dated May 6, 2015.
Final Office Action in U.S. Appl. No. 13/021,950, dated Oct. 22, 2013.
Final Office Action in U.S. Appl. No. 14/860,680, dated Feb. 8, 2018.
Final Office Action on U.S. Appl. No. 14/860,680 dated Dec. 14, 2018.
Final Office Action U.S. Appl. No. 13/021,950, dated Apr. 2, 2018.
Garfield, R.E. et al. (2012) "Use of progesterone and progestin analogs for inhibition of preterm birth and other uterine contractility disorders," FVV in ObGyn 4(4):237-244.
Gil, M. et al. (2010) "Scale-up methodology for pharmaceutical spray drying," Chemistry Today 28(4):18-22.
Guthrie, G.P. et al. (1980) "The in Vivo Glucocorticoid and Antiglucocorticoid Actions of Medroxyprogesterone Acetate," Endocrinology 107(5):1393-1396.
He, D. et al. (2012) "IL-17 Mediated Inftammation Promotes Tumor Growth and Progression in the Skin," PLoS ONE. 7(2):e32126.
Honkanen, J. et al. (2010) "IL-17 Immunity in Human Type 1 Diabetes," J Immunol. 185:1959-1967.
Hueber, W. et al. (2012) "Secukinumab, a human anti-IL-17A monoclonal antibody, for moderate to severe Crohn's disease: unexpected results of a randomized, double-blind placebo-controlled trial," Gut; 61(12):1693-1700.
International Search Report and Written Opinion for International Application No. PCT/US2016/052858, dated Dec. 8, 2016, 10 pages.
International Search Report in International Application No. PCT/US2011/023917, dated Oct. 25, 2011.
Irusen, E. et al. (2002) "p38 Mitogen-activated protein kinase-induced glucocorticoid receptor phosphorylation reduces its activity: Role in steroid-insensitive asthma," J Allergy Clin Immunol. 109:649-657.
Ito, K. et al. (2006) "Mode of Glucocorticoid Actions in Airway Disease," The Scientific World Journal 6:1750-1769.
Janssens, J.P. et al. (1999) "Physiological changes in respiratory function associated with ageing," Eur Respir J. 13:197-205.
Kam, J.C. et al. (1993) "Combination IL-2 and IL-4 Reduces Glucocorticoid Receptor-Binding Affinity and T Cell Response to Glucocorticoids," J Immunol. 151:3460-3466.
Kang, M-J. et al. (2012) "IL-18 Induces Emphysema and Airway and Vascular Remodeling via IFN-g, IL-17A, and IL-13," Am J Respir Crit Care Med. 185(11):1205-1217.
Keenan, C.R. et al. (2015) "Heterogeneity in mechanisms influencing glucocorticoid sensitivity: The need for a systems biology approach to treatment of glucocorticoid-resistant inflammation," Pharmacology & Therapeutics 150:81-93.
Kissi, Y.E. et al. (2014) "Increased Interleukin-17 and decreased BAFF serum levels in drug-free acute schizophrenia," Psychiatry Research 225 (1-2):58-63.
Kuon, R.J. et al. (2010) "Pharmacological actions of progestins to inhibit cervical ripening and prevent delivery depend upon their properties, the route of administration and the vehicle," Am J Obstet Gynecol. 202(5):455.e1-455.e9.
Leung, D.Y.M et al. (1997) "Association of Glucocorticoid Insensitivity with Increased Expression of Glucocorticoid Receptor B," J Exp Med. 186(9):1567-1574.
Loh et al., "Overview of milling techniques for improving the solubility of poorly water-soluble drugs," Asian Journal of Pharmaceutical Sciences, vol. 10, Issue 4, Jul. 2015, 20 pages.
Macintyre, N.R. (2006) "Corticosteroid Therapy and Chronic Obstructive Pulmonary Disease," Respir Care 51(3):289-296.
Mantovani, A. et al. (2008) "Cancer related inflammation," Nature 454(7203):436-444.
Mantovani, G. et al. (1997) "Medroxyprogesterone acetate reduces the in vitro production of cytokines and serotonin involved in anorexia/cachexia and emesis by peripheral blood mononuclear cells of cancer patients," Eur J Cancer 33(4):602-607.
Milner, J.D. et al. (2008) "Impaired TH17 cell differentiation in subjects with autosomal dominant hyper-IgE syndrome," Nature 452(7188):773-776.
Mittelstadt, P.R. et al. (2009) "T Cell Receptor-mediated Activation of p38alpha by Mono-phosphorylation of the Activation Loop Results in Altered Substrate Specificity," J Biol Chem. 284(23):15469-15474.
Morishima, Y. et al. (2013) "Th17-Associated Cytokines as a Therapeutic Target for Steroid-Insensitive Asthma," Clinical and Developmental Immunology 2013:609395, 9 pages.
Newcomb, D.C. et al. (2015) "Ovarian Hormones Increase IL-17A Production from Th17 Cells through an IL-23B and Let-7f Mediated Pathway in Severe Asthma," J Allergy Clin Immunol. pii:S0091-6749(15)00840-4: AB230, Abstract 745.
Nold, C. et al. (2013) "Prevention of preterm birth by progestational agents: what are the molecular mechanisms?" Am J Obstet Gynecol. 208(3):223.e1-223.e7.
Non-Final Office Action in U.S. Appl. No. 13/021,950, dated Apr. 2, 2013.
Non-Final Office Action in U.S. Appl. No. 13/021,950, dated Aug. 27, 2014.
Non-Final Office Action in U.S. Appl. No. 13/021,950, dated Mar. 21, 2016.
Non-Final Office Action in U.S. Appl. No. 13/021,950, dated Sep. 1, 2017.
Non-Final Office Action in U.S. Appl. No. 14/860,680, dated Jul. 24, 2017.
Non-Final Office Action on U.S. Appl. No. 14/860,680 dated Aug. 7, 2018.
Notice of Allowance U.S. Appl. No. 13/021,950, dated May 1, 2018.
Notice of Allowance U.S. Appl. No. 13/021,950, dated Nov. 15, 2018.

(56) References Cited

OTHER PUBLICATIONS

Novartis (2014) Web (https://www.novartis.com/news/media-releases/novartis-announces-fda-approval-first-il-17a-antagonist-cosentyxtm-secukinumab).
Nunez, B. et al. (2011) "Anti-Tissue Antibodies Are Related to Lung Function in Chronic Obstructive Pulmonary Disease," Am J Respir Crit Care Med. 183(8):1025-1031.
Ortiz, M.L. et al. (2015) "Immature myeloid cells directly contribute to skin tumor development by recruiting IL-17-producing CD4 T cells," J Exp Med. 212(3):351-367.
Oshiro, K. et al. (2011) "Interleukin-17A is involved in enhancement of tumor progression in murine intestine," Immunobiology 217(1):54-60.
Park, H. et al. (2005) "A distinct lineage of CD4 T cells regulates tissue inflammation byproducing interleukin 17," Nat Immunol. 6(11):1133-1141.
Patel, Y. et al. (2012) "Hydroxyprogesterone Caproate Injection (Makena) One Year Later, to Compound or Not to Compound—That is the Question," P&T 37(7):405-411.
Pinart, M. et al. (2013) "IL-17A Modulates Oxidant Stress-Induced Airway Hyperresponsiveness but Not Emphysema," PLOS One 8(3):e58452, 1-8.
Poulin et al. (1989) Breast Cancer Res Treatment 13:161.
Rathore, A.M. et al. (2015) Hormones in Obstetrics and Gynaecology, Jaypee Brothers Publishers.
Ringold, H.J. et al. (1956) "Steroids. LXXIII. The Direct Oppenauer Oxidation of Steroidal Formate Esters. A New Synthesis of 17alpha-Hydroxyprogesterone," J Amer Chem Soc 78:816-819.
Romero, R. et al. (2013) "Progesterone is not the same as 17alpha-hydroxyprogesterone caproate: implications for obstetrical practice," Am J Obstet Gynecol. 208(6):421-426.
Roussel, L. et al. (2010) "IL-17 Promotes p38 MAPK-Dependent Endothelial Activation Enhancing Neutrophil Recruitment to Sites of Inflammation," J Immunol. 184:4531-4537.
Ruddock, N.K. et al. (2008) "Progesterone, but not 17-alpha-hydroxyprogesterone caproate, inhibits human myometrial contractions," Am J Obstet Gynecol. 199:391.e1-391.e7.
Saaresranta, T. et al. (2005) "Medroxyprogesterone improves nocturnal breathing in postmenopausal women with chronic obstructive pulmonary disease," Respiratory Res. 6:28.
Saijo, S. et al. (2010) "Dectin-2 Recognition of a-Mannans and Induction of Th17 Cell Differentiation is Essential for Host Defense against Candida albicans," Immunity 32(5):681-691.
Schindler, A.E. et al. (2003) "Classification and pharmacology of progestins," Maturitas 46(S1):S7-S16.
Scott-Moncrieff, J.C. et al. (1990) "Serum disposition of exogenous progesterone after intramuscular administration in bitches," Am J Vet Res. 51(6):893-895.
Seow, C.H. et al. (2015) "Downregulation of IL-17 Related Cytokines in the Second Trimester of Pregnancy Women With IBD Supports Pregnancy Driven Immunomodulatory Effects Involving the Th17 Pathway," Gas. 148(4):S454-S455, Abstract Su1262.
Tan, H-L. et al. (2013) "IL-17 in lung disease: friend or foe?" Thorax 68:788-790.
The Merck Index (2001) Table of Progestogens.
Tsoukas, A. et al. (2015) "Targeting the IL-17/IL-23 Axis in Chronic Inflammatory Immune-Mediated Diseases," Molecular Biology of B Cells (2nd Edition):527-539.
U.S. Food and Drug Administration (2015) "FDA approves new psoriasis drug Cosentyx," Web.
Van Rossum, E.F.C. et al. (2011) "Glucocorticoid Resistance," Endocr Dev. 20:127-136.
Vasanthakumar, R. et al. (2014) "Serum IL-9, IL-17, and TGF-beta levels in subjects with diabetic kidney disease (CURES-134)," Cytokine 72(1):109-112.
Vazquez-Tello, A. et al. (2013) "Glucocorticoid Receptor-Beta Up-Regulation and Steroid Resistance Induction by IL-17 and IL-23 Cytokine Stimulation in Peripheral Mononuclear Cells," J Clin Immunol. 33:466-478.
Vippagupta et al. (2001) Advanced Drug Delivery Rev. 48:3-26.
Vlahos, R. et al. (2014) "Recent advances in pre-clinical mouse models of COPD," Clinical Science (Lond) 126: 253-265.
Vroman, H. et al. (2015) "Mode of Dendritic Cell Activation: The Decisive Hand in Th2/Th17 Cell Differentiation. Implications in Asthma Severity?" Immunobiology 220(2):254-261.
Website Screenshot (2010) (http://www.nlm.nih.gov/medlineplus/immunesystemanddisorders.html).
Wei, J. et al. (2013) "IL-17 cytokines in immunity and inflammation," Emerging Microbes and Infections 2:e60.
Wu, D. et al. (2013) "Interleukin-17: A Promoter in Colorectal Cancer Progression," Clinical and Developmental Immunology 2013:436307.
Yan, R. et al. (2008) "Metabolism of 17alpha-hydroxyprogesterone caproate by hepatic and placental microsomes of human and baboons," Biochem Pharmacol. 75(9):1848-1857.
Yang, N et al. (2012) "Current Concepts in Glucocorticoid Resistance," Steroids 77:1041-1049.
Zijlstra, G.J. et al. (2012) "Interleukin-17A induces glucocorticoid insensitivity in human bronchial epithelial cells," Eur Respir 39:439-445.
Non-Final Office Action issued in U.S. Appl. No. 14/860,680 dated Jul. 5, 2019.
Final Office Action on U.S. Appl. No. 14/860,680 dated Jan. 27, 2020.

* cited by examiner

FIG. 2

| Particle size reduction of 17-OHPC ||||| 
|---|---|---|---|---|
| No of HPH cycles | $D_v10$ (µm) | $D_v50$ (µm) | $D_v90$ (µm) | Span |
| Bulk material | 6.345 | 56.762 | 307.607 | 5.307 |
| 1 | 1.444 | 8.228 | 29.132 | 3.365 |
| 2 | 1.208 | 5.313 | 16.668 | 2.91 |
| 3 | 1.143 | 4.474 | 13.219 | 2.699 |
| 4 | 1.099 | 4.013 | 11.114 | 2.496 |
| 5 | 1.034 | 3.393 | 9.464 | 2.485 |
| 6 | 1.07 | 3.634 | 9.08 | 2.204 |
| 7 | 1.051 | 3.391 | 8.275 | 2.13 |
| 8 | 1.015 | 3.021 | 7.302 | 2.081 |
| 9 | 1.007 | 2.95 | 7.013 | 2.036 |
| 10 | 0.992 | 2.664 | 6.217 | 1.961 |
| 12 | 1.016 | 2.781 | 6.311 | 1.904 |
| 14 | 1.089 | 2.691 | 5.623 | 1.685 |
| 16 | 1.071 | 2.574 | 5.347 | 1.662 |
| 18 | 1.029 | 2.395 | 4.959 | 1.641 |
| 20 | 1.03 | 2.362 | 4.815 | 1.602 |
| 25 | 1.014 | 2.255 | 4.517 | 1.553 |

FIG. 5

Particle size of 17-OHPC in water suspension

| Cycle | Dv10 | Dv50 | Dv90 | Span |
|---|---|---|---|---|
| 25 | 1.078 | 2.78 | 5.626 | 1.636 |
| 40 | 1.07 | 2.521 | 4.862 | 1.505 |
| 55 | 1.197 | 3.720 | 8.322 | 1.915 |

Particle size of 17-OHPC after spray drying (powder)

| Cycle | Dv10 | Dv50 | Dv90 | Span |
|---|---|---|---|---|
| Bulk material | 2.398 | 23.61 | 98.799 | 4.083 |
| 10 | 1.079 | 3.56 | 8.279 | 2.024 |
| 25 | 1.037 | 2.602 | 5.364 | 1.663 |
| 40 | 1.017 | 2.619 | 5.658 | 1.772 |
| 55 | 1.037 | 2.434 | 4.865 | 1.573 |

FIG. 9

Area percentage of impurities for spray dried powders

| Cycle | Bulk | 10 | 25 | 40 | 55 |
|---|---|---|---|---|---|
| 17-HP | 0.05 | 0.04 | 0.04 | 0.04 | 0.05 |
| Unknown | 0.37 | 0.47 | 0.47 | 0.46 | 0.46 |

PULMONARY DELIVERY OF PROGESTOGEN

RELATED U.S. APPLICATION DATA

This is a Continuation-In-Part application of U.S. patent application Ser. No. 13/174,939, filed on Jul. 1, 2011, now pending, which is a Continuation-In-Part application of U.S. patent application Ser. No. 13/021,950 filed Feb. 7, 2011, and claims the benefit of PCT International Patent Application No. PCT/US11/23917, filed Feb. 7, 2011, and U.S. Provisional Patent Application No. 61/302,325, filed on Feb. 8, 2010, the entire disclosures of which are incorporated herein by reference. This Continuation-in-Part application claims benefit of priority to U.S. Provisional Patent Application No. 62/195,649 filed on Jul. 22, 2015, the entire disclosures of which are incorporated herein by reference.

FIELD OF THE INVENTION

The present invention relates, inter alia, to inhalation formulations comprising a progesterone such as 17-alpha-hydroxyprogesterone caproate (17-HPC or 17-OHPC); and methods and kits for administering a progestogen as a glucocorticoid sensitizer to restore corticosteroid sensitivity, in order to treat one or more glucocorticoid insensitivity related diseases or conditions.

The present invention includes the inhalation formulations and methods in the U.S. patent application Ser. No. 13/021,950. The present invention also relates to inhalation formulations and methods for reducing cytokine interleukin-17 (IL-17 or IL-17A) levels in both broncheoalveolar lavage fluid (BALF) and blood/serum involving the use of 17-OHPC. Inhalation formulations and methods containing 17-OHPC may also treat IL-17 cytokine-mediated auto-immune and auto-inflammatory diseases.

The present invention relates to the inhalation formulations, methods and kits in using 17-OHPC in inhibiting phosphorylation (activation) of p38 mitogen-activated protein kinase (MAPK or RK or Cytokinin specific binding protein) in the lungs. Inhalation of 17-OHPC may treat related diseases involving the inhibition of p38 MAPK-mediated phosphorylation.

The present invention relates to the inhalation formulations, methods and kits involving the inhalation of 17-OHPC in combination with other medicines such as the use of a glucocorticoid (GC), for example, budesonide (BUD) or fluticasone. This combinatorial treatment of 17-OHPC and a GC may be used to treat IL-17 cytokine-mediated auto-immune and auto-inflammatory diseases, and with related diseases involving inhibition of p38 MAPK-mediated phosphorylation.

The present invention relates to the inhalation formulations, methods and kits involving the manufacture of 17-OHPC powder that has a particle size suitable for inhalation. The manufacture of 17-OHPC powder involves applying cavitational forces on formulations containing 17-OHPC through repeating cycles of high pressure homogenization followed by spray drying. Particle sizes are reduced to a Mass Median Diameter, or a median of the volume distribution, to 57 µm or less.

The novel features which are characteristic of the invention, both as to structure and method of operation thereof, together with further objects and advantages thereof, will be understood from the following description, considered in connection with the accompanying drawings, in which the preferred embodiment of the invention is illustrated by way of example. It is to be expressly understood, however, that the drawings or figures are for the purpose of illustration and description only, and they are not intended as a definition of the limits of the invention.

GENERAL BACKGROUND AND STATE OF THE ART

Pharmaceutical Micronization.

Achieving desirable dry powder characteristics, such as granule size and purity, is critical for optimal performance of a pharmaceutical inhalant comprising of an active ingredient. Therefore, appropriate micronization of a drug or an active pharmaceutical ingredient (API) is an integral part of manufacturing. "Bottom-up" approaches such as crystallization, spray drying, ionic complexation, and precipitation of dissolved active pharmaceuticals may be performed. Though simple and cost effective, a disadvantage of the "bottom-up" approach is the difficulty in controlling particle size and shape. Lonare A. A., et al., Int J Chem Eng App. 2013 Vol. 4(5): 337-341, Chikhalia V., et al., EurJ Pharm Sci. 2006 January; 27(1):19-26.

An alternative method to obtain desired particle size and shape is the "top-down" approach. The "top down" approach involves the mechanical reduction of previously formed larger particles to the desired size. Supra Lonare A. A. et al. The mechanical reduction process relies on milling and/or grinding and includes techniques such as wet milling, dry milling, ball/pearl milling, spiral media milling, jet milling, high pressure homogenization (HPH), or any other form of impact milling known in the art. Supra Lonare A. A. et al.; Nakach M., et al., Int J Min Proc. December 2004. 74: S173-181. As discussed further below, these techniques require high input energy, which may cause shear and heat, thus leading to potentially undesirable polymorphisms, amorphisation, denaturation, and loss of activity. Also, these methods may allow the particles to frequently contact portions of the milling equipment which may lead to equipment erosion and impurities within the particles. Nonetheless, milling and/or grinding have been the commonly employed techniques for the preparation of pharmaceuticals.

Milling Technology.

There are two basic technologies that are used for preparing pharmaceutical powders; bead/pearl milling and HPH. Keck C. M. et al., Eur J Pharm Biopharm. 2006 January; 62(1):3-16. More recently, combinative technologies have also been implemented that rely on a pre-treatment size reduction process, such as spray-drying or freeze drying, before the top-down process is performed. Möschwitzer J. P. Int J Pharm. 2013 Aug. 30; 453(1):142-56.

Bead Milling.

Bead milling (also known as pearl milling or wet ball milling) is a process of preparing pharmaceutical suspensions by grinding in a chamber, for example a cylindrical chamber. The chamber is filled with a pharmaceutical drug along with a grinding/milling medium such as beads/balls made from ceramic, glass, plastic, stainless steel, or polystyrene derivatives, or zirconium salts. Movement of the milling medium for example by rotation of the cylindrical chamber causes shear forces during impaction of the milling medium with the pharmaceutical drug, and such shear forces causes fracture of the pharmaceutical drug. Nekkanti V., et al., The Delivery of Nanoparticles ISBN:978:953-51-0615-9; Khadka P., et al., Asi J Pharm Sci. 2014 December (9)6:304-316. Particle sizes achieved by ball milling have been reported to be between 100 and 300 nm. Supra Möschwitzer J. P. However, "erosion from the milling material during the milling process is a common problem of this technology", thereby introducing impurities into the particles. Shegokar R., et al., Int J Pharm. 2010 Oct. 31; 399(1-2):129-39.

High Pressure Homogenization.

High pressure homogenization is a "particle size reduction [technique] that utilizes high-shear processing of an aqueous slurry of drug and stabilizing agents". Sharma P. H., et al., *Eur. J. Pharm. Med. Res.* 2015, 2(2), 484-502. The HPH milling method includes three types of homogenization processes; Microfluidizer jet milling (IDD-P™ technology) which is based on the jet stream principle, in water piston-gap homogenisers (Dissocubes® technology), and in water-reduced/non-aqueous media piston-gap homogenisers (Nanopure® technology). Junghanns J. A. H. et al. Int J Nanomedicine. 2008 September; 3(3): 295-310; Supra Shegokar R. et al.

Jet Milling.

Jet stream homogenizers, such as the Microfluidics Inc. Microfluidizer®, rely on "frontal collision of two fluid streams in a Y-type or Z-type chamber under pressures up to 1700 bar" to generate small particles. Supra Shegokar R. et al. The collision between the two jet streams results in shear and cavitation forces which lead to particle size reduction.

Jet mills use highly pressurized air to grind pharmaceuticals. At times, the term "fluid" jet mill is used to refer to a jet milling process with the fluid being high pressurized air. Supra Khadka P. et al. The energy of the fluid grinds the pharmaceutical into powder. Advantages of jet milling include that jet milling can be a dry process, can result in the preparation of micron-sized particles with a narrow size distribution, may have an absence of contamination, and may be suitable for heat sensitive pharmaceuticals. Id. Alternative jet milling procedures employ the use of water, for example water jet milling. Water jet milling creates cavitation zones which "disintegrate particles by dynamic impact of liquid on particle surface without a direct contact with milling bodies and inner surfaces". Dvorsky R., et al., Adv Pow Tech. 2011(22):639-643. Unfortunately, jet milling requires "a relatively high number of cycles (50-100 passes)" which are necessary to obtain sufficient particle size reduction". Supra Shegokar R. et al.

Piston-Gap Homogenizers.

Piston-gap homogenizers, such as the DissoCubes® (SkyePharma PLC), rely on forcing an aqueous solution under high pressure through a thin gap, for example, a 5-20 µm gap. Supra Dvorsky R. As the aqueous solution passes through the gap, there is an increase in dynamic pressure which is simultaneously compensated by a reduction in static pressure, thus causing the solution to boil. Upon exiting of the solution from the gap, the bubbles from boiling collapse under normal atmospheric pressure, and undergo cavitation. Id. The cavitation forces of HPH are responsible for inducing particle size reduction.

Nanopure® technology by PharmaSol GMBH, Berlin, now Abbott Laboratories, is a piston-gap homogenization process that uses dispersion medium with a low vapor pressure (i.e. oils, PEG, water-reduced or non-aqueous media) and optionally homogenization at low temperature. Supra Shegokar et al., Supra Junghanns J. A. H., et al. Thus, this process may be used for temperature labile and hydrolysis sensitive pharmaceuticals.

Control Parameters.

Control parameters for achieving desirable size, shape, density, dispensability, agglomeration, aerodynamic properties, and stability during a given milling procedure not only include choosing the type of milling equipment, but may also include a precise understanding of temperature, pressure, duration of milling, and number of milling cycles performed. All of which have an influence on the powder granulometry of a particular pharmaceutical. Furthermore, a person having ordinary skill in the art knows that a method of particle processing and size reduction of any active pharmaceutical ingredient (API) cannot easily be predicted to produce a particle of proper structure and effectiveness. With regards to using different milling processes, "[d]ifferent equipments have their pros and cons, but experience is required to select the right one . . . [m]aterial characterization of the drug substance needs to be associated with the micronisation technique to have a clear pictures of the size, shape and crystallinity of the powder." Larran J. M., et al., Pharm Man Pack Sou, Spring 2005. Vehring R. teaches that particle size reduction is a complex engineering process that is "difficult to design using an empirical approach alone because of the many processes and formulation variables that need to be tuned correctly to achieve the desired result". Vehring R., Pharm Res. 2008(25)5:999-1012.

HPH Milling Cycles and Particle Size Reduction.

Size reduction using HPH depends on the power density of the homogenizer, the temperature, number of homogenization cycles, and pressure which has a relatively small effect on decreasing the size of a pharmaceutical but a significant effect on particle size distribution. Supra Keck C. M. et al., Supra Nekkanti V. et al. With respect to cycles, the fluid passing through the HPH gap occurs within several milliseconds, which is not sufficient time to comminute pharmaceutical crystals into a uniform size. Hence, it is necessary to perform "five, ten, or more cycles depending on the hardness of [the] drug and desired particle size". Junyaprasert V. B. et al., Asian J Pharm Sci. 2015(10)1:13-23.

For example, milling cycles to obtain span values in the approximate range of 1.4 to 2.0 for fluticasone propionate, salmeterol xinafoate, and titropium bromide are 20, 7, and 21 cycles, respectively. See Gil et al., U.S. patent application Ser. No. 13/642,397. There has also been teaching that milling over 20 cycles may be damaging to particles, such as in the case of microfluidisation of PEG-PLGA. Sani S. N. et al. *J Microencap*, 2009 September; 26(6):556-561. PEG-PLGA particle size reduction is limited to 5 milling passes (i.e. cycles), and specifically up to 20 passes. Beyond 20 cycles causes agglomeration and variable size distribution of particles, and is "evidence that over-processing and excessive shear stress placed upon nanoparticles is likely to be detrimental upon the size distribution and morphology of the [nano] particles". Id.

Therefore, it is well known by one with ordinary skill in the art that experimentation with regards to the optimal number of homogenization cycles varies for each composition, and substantial testing is required for achieving a desirable size of an API. Thus, the number of milling cycles required for the desired preparation of pharmaceutical formulations cannot simply be extrapolated from one teaching to the preparation and formulation of other APIs.

Furthermore, continuously increasing HPH cycle numbers was believed to not further reduce particle size. Keck C. M. et al. teaches that the reduction of particle size is due to breaking of particles/crystals at weak points (i.e. imperfections), and thus the remaining crystals become more perfect with a reduction of particle size. With every subsequent milling cycle, there are less weak points in a particle that are available to further reduce its size. "[T]he particles will not further diminish, even when additional homogenization cycles are applied." Supra Keck C. M. et al. Keck C. M. et al. shows that the maximum reduction of the mean diameter for azodicarbonamide is asymptotically achieved after five homogenization cycles, with higher cycles only reducing the width of any remaining large crystals. Id.

Furthermore, "particle size reduction effectiveness of [milling] depends more on the physico-chemical properties of the processed drug", and therefore, each milling process used to micronize any API requires empirical evaluation. Supra Möschwitzer J. P. Additionally, experimentation of formulation performance is also required for scale-up production, as there is "no framed algorithm which can help the formulators predict the large scale performance of a product based on its small scale behavior." Srivalli K. M. R. et al. *Saudi Pharm J*, May 2014. Therefore, every API requires experimental evaluation and material characterization to determine the most optimal milling procedure and associated operational parameters.

Sources of Impurities.

A possible source of contamination and introduction of impurities and undesirable components into pharmaceutical preparations prepared by HPH is from direct contact with milling parts leading to abrasion and wearing of HPH equipment. For example, wear and tear of the tip of the homogenization valve may lead to reduction of process efficiency. Therefore, ceramic tips may be used in modern homogenizers as a means to decrease contamination and maintain process efficiency. Also, the cavitation process of particle size reduction minimizes direct contact between a drug and milling parts, reducing the potential of contamination to acceptable limits. For example, Krause et al. reported that a nanosuspension of the drug RMKK98 prepared by HPH contained less than 1 ppm of iron after 20 cycles at 1500 bar, which falls well below the 10 ppm acceptable limit. Krause K. P., et al. Int J Pharm. 2000 Mar. 10; 196(2):169-72.

Crystallinity and Amorphous State.

In an ideal crystal, the atoms are arranged in a symmetrical structure resulting in a stable system with distinct physical properties. The crystalline arrangement of an API allows for increased chemical and physical stability. On the contrary, amorphous solids have a non-crystalline molecular order. The lack of a crystalline lattice increases the surface area and in turn increases exposure to the environment which may increase the apparent solubility. However, due to the increased surface area, "hygroscopicity, air oxidation, adsorption on excipients, and/or instrumentation and blending effects are more problematic with amorphous drugs." Bauer J. F. J Valid Tech; August 2009, 15(3)63-68. Thus, maintaining a crystalline structure of an API during the manufacture process is warranted when an increased stability and shelf-life is desired.

The milling process may induce undesirable structural changes in the pharmaceutical ingredient and result in structural variability and impurities. It is well known that milling methods, such as dry milling and ball milling, induce active pharmaceutical ingredients to lose their crystalline form to an anhydrous or amorphous form of the active ingredient. U.S. patent application Ser. No. 13/642,397, Gil et al. "Milling can reduce the crystallinity of a drug and create areas of disorder or amorphous regions; [and] total change to the amorphous state is possible". Supra Bauer J. F. For example, progesterone is known to exist in two polymorphic forms; form 1 (α-form) and form 2 (β-form). Araya-Sibaja A. M., et al., Pharm Dev Technol. 2014 November; 19(7):779-88. The stress of mechanical grinding of progesterone form 2 induces its polymorphic transformation into progesterone form 1. Therefore, since milling may influence the crystallinity and amorphous state of a pharmaceutical drug, experimentation is necessary to identify milling parameters that produce a desirable polyphorm.

Inhalant Particle Size.

The optimal size of a particle suitable for inhalation is between approximately 1-5 µm. Siew A. *Pharm Technol.* 2014(38):2. For example, salbutamol aerosols with a mass median aerodynamic diameter (MMAD) of 2.8 µm produced superior bronchodilation, while the optimal particle size for a $\beta_2$ antagonist was shown to be approximately 3 µm. Labiris et. al., Br J Clin Pharmacol. 2003 December; 56(6): 588-599. Particles greater than 10 µm are deposited in the oropharyngeal region and settle on the larynx, and are subsequently swallowed having a minimal to no therapeutic effect. Id. Particles with a size of 5-10 µm are mainly deposited in the oropharayngeal region, while particles of 1-5 µm in diameter are deposited in the small airways and alveoli. Id. Particles with an MMAD of less than 0.5 µm deposit via diffusion, however, particles of the size of 0.5 µm may fail to deposit and be exhaled. Id. The desirable size range of pharmaceutical particles intended for therapeutic use by inhalation is between 1-5 µm. Particle sizes between 5-15 µm are suggested for nasal delivery, with a recommendation of 9 µm in order to avoid lung inhalation of drugs intended for nasal delivery. Djupesland P. G. Drug Deliv Transl Res. 2013 February; 3(1):42-62.

Inhalant Span Value.

The span value of the power (or polydisperity) must also be accounted for in preparing an effective inhalant. The span value is the width of the distribution of the particle size as defined below. Too broad of a span value may result in impaction or retention within the inhaler, thereby reducing the effective dosage necessary for treatment. Chew et al. J Pharm. Pharmaceut. Sci., 2002 5(2) 162-168. An ideal span value is 2.5 or less. U.S. patent application Ser. No. 13/642, 397, Gil et al.

Achieving a desirable particle size suitable for inhalation while maintaining crystallinity, purity, and activity requires experimentation and validation for every API. There has been no method to prepare an inhalant containing 17-OHPC of proper particle size, span, structure, and purity.

SUMMARY OF THE INVENTION

The present invention is directed to inhalant formulations and methods for restoring corticosteroid sensitivity or reversing the glucocorticoid insensitivity or enhancing glucocorticoid sensitivity.

Other embodiments of the present invention are directed to inhalation formulations comprising a progestogen such as 17alpha-hydroxyprogesterone caproate for pulmonary delivery.

Yet other embodiments of this invention are directed to inhalation formulations comprising a progestogen such as 17alpha-hydroxyprogesterone caproate and budesonide for pulmonary delivery.

Yet other embodiments of this invention are directed to inhalation formulations comprising a progestogen such as 17alpha-hydroxyprogesterone caproate and fluticasone for pulmonary delivery.

It is understood that the embodiments above are provided as representative embodiments of the present invention, and in no way are to be constructed as limiting the scope of the present invention.

BRIEF DESCRIPTION OF THE DRAWINGS

FIG. 2 shows exemplary particle size distribution values of 17-OHPC after increasing HPH cycles.

FIG. 5. shows an exemplary particle size distribution values of 17-OHPC after HPH in water and after spray drying.

FIG. 9 is an exemplary area percentage of impurities of bulk and spray dried 17-OHPC as determined from HPLC data.

DEFINITIONS

Figure 1:
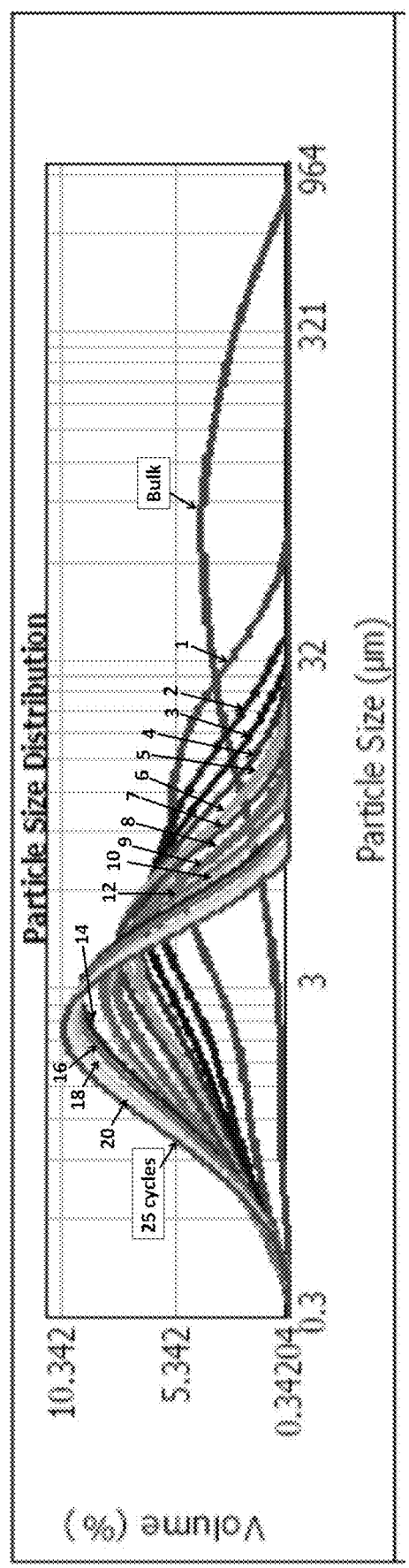
FIG. 1 is an exemplary comparison of particle size distribution profiles of 17-OHPC versus high pressure homogenization cycles.

As used herein, the term "glucocorticoid insensitivity" is intended to include, but is not limited to, corticosteroid resistance, corticosteroid dependence, corticosteroid refractory responses, corticosteroid intolerance, and other types of corticosteroid ineffectiveness. It has been recognized that several distinct molecular mechanisms contribute to decreased anti-inflammatory effects of glucocorticoids. Different inflammatory diseases may share similar molecular mechanisms, and a single disease may have a heterogeneity of mechanisms.

"Corticosteroid resistance" to the anti-inflammatory effects of corticosteroids is defined as no clinical improvement after treatment with high-dose glucocorticoid.

"Corticosteroid dependence" is defined as a condition that initially responds to corticosteroids but relapses quickly upon drug withdrawal or dose tapering.

"Corticosteroid refractory response" is defined as a condition that does not respond to an adequate induction dose of corticosteroids. It includes relatively or totally refractory responses to glucocorticoid therapy, and often needs to be controlled by add-on treatment.

Other types of "corticosteroid ineffectiveness" includes the need for a very high dose treatment, "difficult to treat" and "do not respond well" or severe cases, and impaired in vitro and in vivo responsiveness.

"Corticosteroid intolerance" is defined as toxicity of the therapy and/or risks for developing corticosteroid-related adverse events such as opportunistic infections and bone loss.

"Glucocorticoid sensitizer" is defined as a pharmaceutical agent and product that has a function in restoring corticosteroid sensitivity, enhancing glucocorticoid sensitivity, reversing the glucocorticoid insensitivity, and protecting against loss of glucocorticoid sensitivity, and used for treating, preventing, or ameliorating one or more of the symptoms of diseases or disorders associated with glucocorticoid insensitivity (e.g., corticosteroid dependent or corticoid resistant or unresponsive or intolerant to corticosteroids). Therapeutic effects of the use of a glucocorticoid sensitizer include any, but are not limited to, steroid-sparing in corticosteroid-dependent patients, better responsiveness or tolerance to corticosteroids, achieving efficacy by using a lower dose of corticosteroid, preventing individuals at risk for developing refractory responses or resistance or exacerbations in response to antigen exposures, infections, exercise, or irritants, achieving optimal immune functions, easier responses for the subject or patient when steroid administration is tapered or withdrawn, or after prolonged administration of corticosteroids, decreased risks for developing corticosteroid-related adverse events such as opportunistic infections, bone loss, pathologic fracture, diabetes, cataract, and combinations thereof.

As used herein, the term "progesterone" or "P4" refers to the chemical compound with systematic name pregn-4-ene-3,20-dione, Chemical Abstracts Services (CAS) number 57-83-0.

As used herein, the term "17α-hydroxyprogesterone caproate" or "17-OHPC" refers to the chemical compound with systematic name 17-[(1-Oxohexyl)oxy]-pregn-4-ene-3,20-dione, CAS Registry Number 630-56-8.

Unless otherwise noted, the term "Interleukin-17" or "IL-17" as used herein, refers to the cytokine protein "IL-17A". Wherein "IL-17A" refers to the protein of any IL-17A protein sequence known in the art.

As used herein, the term "p38" refers to any of the p38 isoforms known in the art, namely, p38α (MAPK14), p38β (MAPK11), p38γ (MAPK12/ERK6), or p38δ (MAPK13/SAPK4), unless otherwise specifically noted.

As used herein, the term "R-group" refers to any combination of carbon, hydrogen, oxygen, nitrogen, and/or halogen atoms attached to the C-17 position on the cholesterol hydrocarbon ring framework.

As used herein, the term "patient" refers to a human receiving or registered to receive medical care or treatment.

As used herein, the term "severe asthma" or "corticosteroid resistant asthma" or "therapy resistant asthma" refers to asthma symptoms and exacerbations that are unresponsive or respond suboptimally to inhaled or systemic corticosteroids resulting in a reduction in effectiveness of corticosteroids in controlling asthma. Bhaysar P. et. al. states that suboptimal response in corticosteroid resistant asthma is "defined as <15% of baseline forced expiratory volume in 1 s ($FEV_1$) after taking prednisolone (30-40 mg/day) over 14 days while demonstrating marked bronchodilator response to inhaled $\beta_2$ agonists" as compared to patients with corticosteroid responsive asthma who demonstrate "a >25% improvement in $FEV_1$ after prednisolone treatment". Bhaysar P. et al., 2008 September; 63(9):784-90. Corticosteroid resistant asthma patients also show "a reduction in suppressive effect of dexamethasone on the proliferative response of or release of neutrophil activating factor from peripheral blood mononuclear cells (PMBCs) has been observed". Id. Also, severe asthamtics have increased levels of active p38 than non-severe asthma patients. Id. Furthermore, "decreased glucocorticoid responsiveness is found in patients with severe asthma and asthmatics who smoke, as well as in all patients with COPD and cystic fibrosis". Barnes P. J., J Steroid Biochem Mol Biol. 2010 May 31; 120(2-3):76-85. Mild intermittent asthma may be controlled by $\beta_2$ agonists alone while moderate to severe asthma may necessitate the use of high-dose inhaled or oral corticosteroids. Stirling R. G., et. al., Allergy 2001:56:825-840.

As used herein, the term "inhalation" refers to inhaling or breathing as a route of administration of a pharmaceutical composition through respiratory passages, wherein delivery of said pharmaceutical composition may preferably be, for example, via an aerosol spray, a powder mixture, gas, or vapor in a pressurized pack or nebulizer or in an inhaler.

As used herein, the term "fine particle dose" (FPD) refers to the dose of aerosolized particles with an aerodynamic diameter of less than five microns. Fine particle fraction (FPF) is defined as the ratio of FPD to the total recovered dose.

As used herein, the term "high pressure homogenization" refers to any milling technique/technology that employs cavitation forces for reducing particle size, including any piston-gap homogenizers. Examples of HPH technology include, but are not limited to, jet stream homogenizers, microfluidizers, and piston-gap homogenizers. Examples of HPH technologies include, but are not to, IDD-P™, Nanopure®, Microfluidizer®, and DissoCubes®.

As used herein, the terms Dv10, Dv50, and Dv90 refer to the standard percentile readings of particle size analysis performed by an optical measuring g unit such as, but not limited to, a Malvern Mastersizer 2000S. Dv50 refers to the size in microns at which 50% of the sample is smaller and 50% is larger. This value is known as the Mass Median Diameter (MMD) or the median of the volume distribution. The v in the expression shows that this refers to the volume distribution, Dv10 is the size of particle below which 10% of the sample exists. Dv90 is the size of the particle below which 90% of the sample exists. As used herein, the term span refers to a measurement of width distribution and is calculated using the formula (Dv90-Dv10) Dv50. The narrower the distribution, the smaller the span value. Malvern Instruments Ltd. Mastersizer 2000 user manual (2007).

DETAILED DESCRIPTION OF THE INVENTION

A particularly preferred route of delivery for administering effective amounts of the progesterone compounds or compositions containing therapeutically effective concentrations of the compounds is via an inhalation route of administration. When an inhalation route of administration is used, delivery may preferably be, for example, via an aerosol spray or powder mixture in a pressurized pack or a nebulizer or in an inhaler.

Inhalation formulations may be used for the treatment of glucocorticoid-insensitivity related diseases or disorders, or conditions as previously provided in the U.S. patent application Ser. No. 13/174,939. Inhalation formulations may also be used for treating IL-17 cytokine-mediated auto-immune and auto-inflammatory diseases. For example, IL-17 has been linked to numerous inflammatory and auto-inflammatory diseases such as autoimmune and type-1 diabetes (Emamaullee J. A. et al., Diabetes 2009, 58:1302-1311, and Kudo et al., Nat. Med. 2012, 4; 18(4):547-54), end-stage kidney disease (Kim Y. G. et al., Am. J. Nephrol. 2012, 36:472-477), obliterative bronchiolitis post-lung transplant (Suzuki H. et al., J. Immunol. 2013, 191:4431-4439), asthma (Busse W. W. et al., Am J respire Crit Care Med 2013, 188 (11): 1294-1302), encephalomyelitis (Knier B. et al., J. Autoim. 2015, 56:34-44), pulmonary fibrosis (François A. et al., J. of Autoimmun. 2015, 56: 1-11), liver fibrosis (Amara S. et al., Mol. Immunol., 2015, 64: 26-35), chronic obstructive pulmonary disease (Caramori G. et al., Intl. J. of COPD 2014, 9:397-412), preeclapsia (Cornelius D. C. et al., Pregnancy Hypertens. 2015, 5 (1): 17), parenchymal lung fibrosis (Martinu T. et al., J. Heart and Lung Transpl., 34:4, 2015, 175-6), atherosclerosis (Gong F. et al., Cell Immunol. 2015 September; 297(1):33-9), rheumatoid arthritis (Konya C. et al., Cytokine. 2015 October; 75(2): 207-15), systemic lupus erythematosus (Id.), psoriasis (Id.), lupus nephritis (Qiao G. et al., Clin. Immunol. 2015, 157(2): 166-174), inflammatory bowel disease (Fujino S. et al., Gut 2003; 52:65-70), Crohn's disease (Hueber W. et al., Sci Transl Med. 2010 Oct. 6:2(52):52ra72), multiple sclerosis (Gold R. et al., Am. J. Pathol. 2008; 172(1): 8-10), Duchenne muscular dystrophy (De Pasquale L. et al., Neurology. 201278(17):1309-14), and psychiatric disorders such as schizophrenia and depression (Potvin S. et al., Psychiatry 2008; 63(8):801-8, and Roy T. et al., J Affect Disord. 142 Suppl: S8-21).

Exemplary 17-OHPC Powder Formulations.

As described herein, when an inhalation route of administration is used, delivery may preferably be accomplished, for example, via an aerosol spray or powder mixture in a pressurized pack or a nebulizer or in an inhaler.

It is preferred that pharmaceutically acceptable compositions for inhalation delivery include dry powders comprising an active ingredient (for instance, 17-OHPC) present in a dry bulking powder suitable for dry powder inhalation or suspensions suitable for nebulization, and aerosol propellants suitable for use in a metered dose inhaler.

One particularly preferred exemplary formulation is a 17-OHPC powder formulation for dry powder inhalation. Moreover, it is preferred that the 17-OHPC powder formulation for administration by inhalation comprises the 17-OHPC active substance and a pharmaceutically acceptable excipient (e.g., lactose, Respitose ML001, and Lactohale LH300). It is also preferred, according to one embodiment of the present invention, that the composition has the form of a physical mixture (for instance, a powder blend) and comprises from about five (5) to about fifty (50) weight percent of the excipient, and wherein the active substance (17-OHPC) has a particle size distribution profile of from about one nanometer to about ten (10) microns (μm), and wherein the excipient has a particle size distribution of from about fifteen (15) to about five-hundred (500) microns. It is to be understood, in accordance with other embodiments of the present invention, that the compositions of the present invention can alternatively have other particle size distribution profiles as needed or desired, wherein said compositions are suitable and effective for administration to a subject, for instance, administration by inhalation.

Pulmonary local delivery of 17-OHPC and progesterone to a subject (for instance, a human) is preferably accomplished by inhalation through the mouth. Surprisingly, it has been found in accordance with the present invention that respiratory (i.e., inhalation or pulmonary) delivery of the 17-OHPC active ingredient is safe, in contrary to the previous conventional belief that 17-HPC and progesterone are harmful if they are inhaled. This surprising and unexpected finding, in accordance with the present invention, represents a significant discovery.

Moreover, another surprising and unexpected finding, in accordance with the present invention, is that particle size reduction of 17-OHPC to a particle size distribution that ranges from about one nanometer to about ten (10) microns is optimal for a therapeutically effective powder composition (e.g., powder blend). According to certain preferred aspects of the invention, particle size reduction of 17-OHPC, for instance, preferably substantially hydrophobic 17-OHPC, can be achieved by milling in water, either with a surfactant or without a surfactant, wherein the particle size reduction of 17-OHPC is achieved without changing its basic crystalline structure and without generating any measurable additional impurity or impurities.

In addition, it has also been surprisingly discovered, in accordance with the present invention, that one or more pharmaceutically acceptable surfactants may be used in achieving optimal particle size reduction, i.e., the reduction in API particle size, for instance, 17-OHPC particle size reduction. One preferred surfactant is Tween 80, which can preferably be used at a concentration of from about five (5) to about fifteen (15) percent. In addition to Tween 80, other examples of pharmaceutically acceptable surfactants that may be used in accordance with the present invention include, but are not limited to, e.g., monoglycerides, diglycerides, polysorbate 60, sorbitol-fatty acid esters, and glycerol-lactic acid esters. Additional examples of surfactants include, but are not limited to, polyoxyethylene (hereinafter abbreviated as POE-branched alkyl ethers such as POE-octyldodecyl alcohol and POE-2-decyltetradecyl alcohol, POE-alkyl ethers such as POE-oleyl alcohol ether and POE-cetyl alcohol ether, sorbitan esters such as sorbitan monooleate, sorbitan monoisostearate and sorbitan monoleate, POE-sorbitan esters such as POE-sorbitan monooleate, POE-sorbitan monoisostearate and POE-sorbitan monolaurate, fatty acid esters of glycerol such as glyceryl monooleate, glyceryl monostearate and glyceryl monomyristate, POE-fatty acid esters of glycerol such as POE-glyceryl monooleate, POE-glyceryl monostearate and POE-glyceryl monomyristate, POE dihydrocholesterol ester, POE-hardened castor oil, POE-hardened castor oil fatty acid esters such as POE-hardened castor oil isostearate, POE-alkylaryl ethers such as POE-octylphenol ether, glycerol esters such as glycerol monoisostearate and glycerol monomyristate, POE-glycerol ethers such as POE-glycerol monoisostearate and POE-glycerol monomyristate, polyglycerol fatty acid esters such as diglyceryl monostearate, decaglyceryl decastearate, decaglyceryl decaisostearate and diglyceryl diisostearate and other nonionic surfactants; potassium salts, sodium salts, diethanolamine salts, triethanolamine salts, amino acid salts and other salts of higher fatty acids such as myristic acid, stearic acid, palmitic acid, behenic acid, isostearic acid and oleic acid, the above alkali salts of ether carboxylic adds, salts of N-acylamino adds, N-acylsalconates, higher alkylsulfonates and other anionic surfactants; alkylamine salts, polyamine, aminoalcohol fatty acids, organic silicone resin, alkyl quaternary ammonium salts and other cationic surfactants; and lecithin, betaine derivatives and other amphoteric surfactants. It is to be understood that other surfactants may also be used.

In preferred embodiments of the present invention, 17-OHPC compositions include dry powders that comprise the 17-OHPC present in a dry bulking powder suitable for dry powder inhalation; or suspensions comprising 17-OHPC suitable for nebulization, or alternatively, aerosol propellant formulations suitable for use with a metered dose inhaler. It is preferred to achieve a fine-particle dose (FPD) of 17-OHPC in the range of approximately about fifteen (15) to about nine-hundred ninety (990) micrograms (µg), wherein FPD is defined as the dose of the aerosolized drug particles with an aerodynamic diameter less than about five (5) microns.

Figure 10:
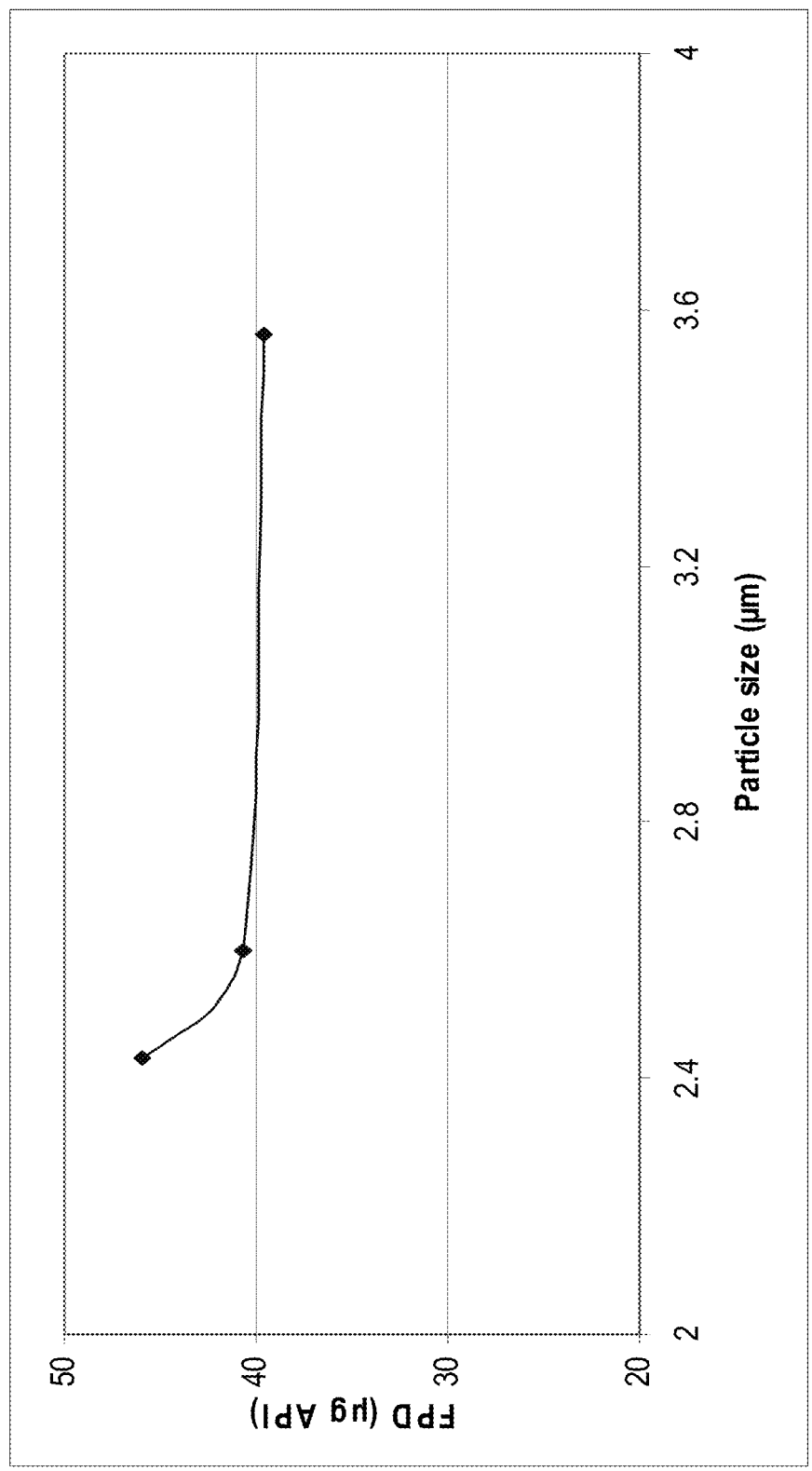
FIG. 10 depicts exemplary results showing a good correlation between 17-OHPC particle size and fine-particle dose (FPD).
Figure 11:
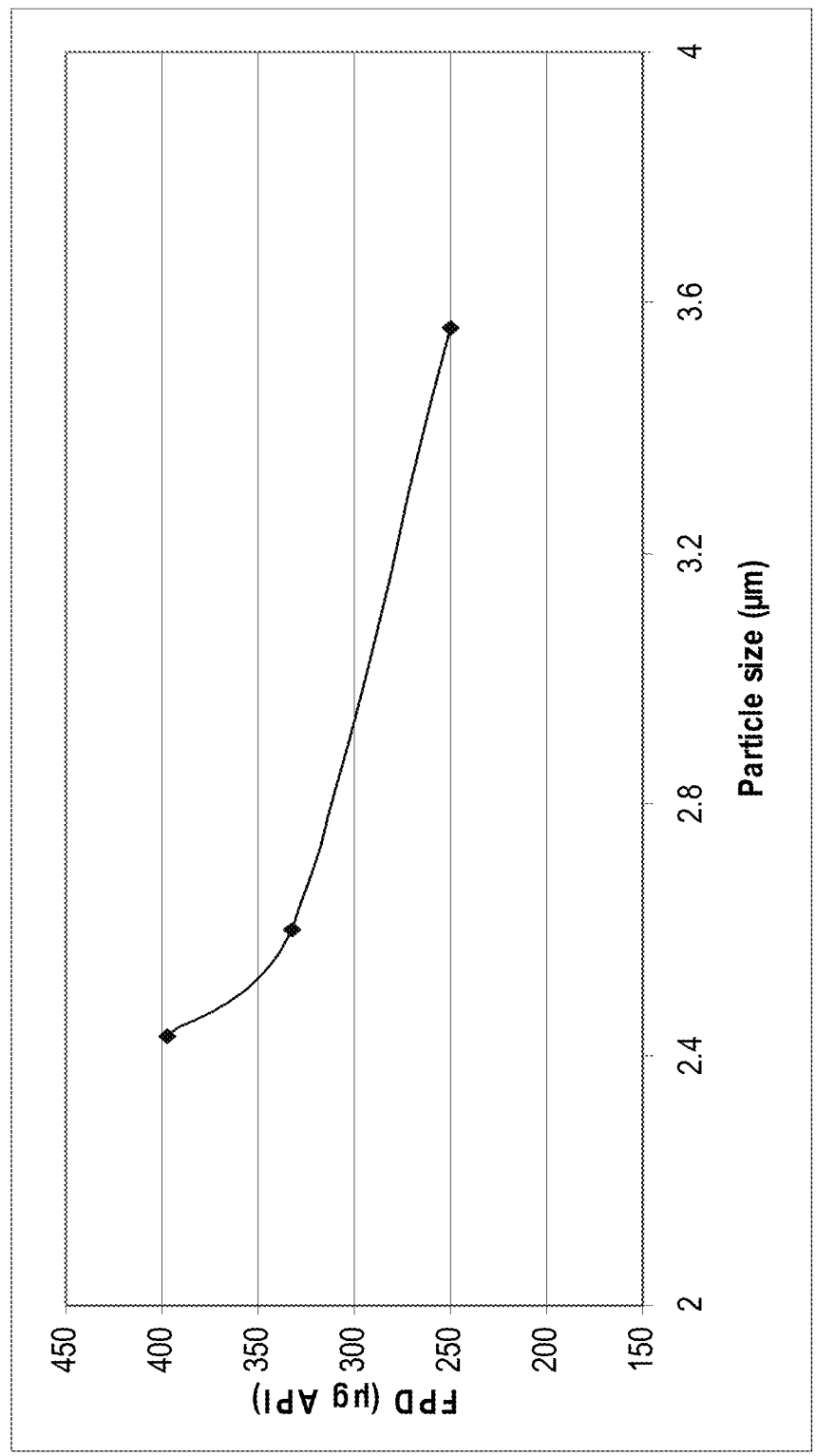
FIG. 11 depicts additional exemplary results showing good correlation between 17-OHPC particle size and fine-particle dose (FPD).

In preferred embodiments of the present invention, and referring to FIGS. 10 and 11 the composition for inhalation delivery exhibits a desired correlation such that a relatively small particle size distribution (for instance, less than about 3.6 microns) correlates with a desired fine-particle dose (FPD) of 17-OHPC, e.g., FPD in the range of between about fifteen (15) to about six-hundred (600) micrograms (µg).

Moreover, it is preferred that the compositions of the present invention are characterized by a blend homogeneity having a relative standard deviation (RSD) less than about five percent, and it is also preferred that the compositions for inhalation delivery have a fine particle fraction (FPF) of about thirty percent or greater. It is also to be understood that blend homogeneity can be determined by any suitable method, for instance, by high-performance liquid chromatography (HPLC).

Exemplary Techniques for Bulk Material Characterization.

For purposes of characterizing bulk material used, for instance, in a powder formulation, e.g., a 17-OHPC powder formulation, any suitable technique or method can be used in accordance with the present invention for characterizing the bulk material, Characterization of the bulk material can be performed, for instance, using bulk powder density analyzers; X-Ray Powder Diffraction (XRPD); water vapor sorption; or dynamic vapor sorption (DVS) techniques.

XRPD is an established and very reliable technique for determining crystalline structure.

Dynamic vapor sorption (DVS) is a gravimetric technique that measures how quickly and how much of a solvent is absorbed by a sample, such as a dry powder absorbing water. DVS accomplishes this by varying the vapor concentration surrounding the sample and measuring the change in mass which this produces.

Exemplary Techniques for Characterizing Particle Size and Distribution.

In accordance with the present invention, any suitable technique or method can be used for characterizing particle size and particle size distribution, for instance, the particle size distribution of an active pharmaceutical ingredient (API) in a powder formulation. Exemplary methods include, for instance, the use of one or more of surface area analysis, pore size analysis, continuous-imaging particle analysis, powder characterization, diffraction laser particle size analysis; pattern recognition techniques; and imaging particle analysis, just to name a few examples. Imaging particle analysis systems, for instance, with laser-scatter triggering, can accurately calculate concentrations of particles in relatively concentrated samples. For sparse samples, methods using a laser-scatter trigger signal can be used to image and measure particles in a sparse sample.

Pattern recognition techniques can also be used to identify and differentiate different particle types contained in a heterogeneous solution. Pattern recognition techniques may involve, for instance, imaging microscopic particles in real-time as they flow in a solution, segregating each individual particle as a separate image, and then applying pattern recognition techniques to differentiate the individual particle types.

Laser diffraction instrumentation may also be used for characterizing particle size and particle size distribution. Particle size and particle size distribution can be determined from a detected diffraction pattern using an appropriate scattering model.

In determining and characterizing particle size, e.g., particle size of an API (active pharmaceutical ingredient) the particle size parameters $Dv(10)$, $Dv(50)$ and $Dv(90)$ may be used. Particle size measurements are preferably expressed in terms of $Dv(10)$, $Dv(50)$, and $Dv(90)$, wherein $Dv(10)$ refers to the particle size below which 10% of the volume of material exists; $Dv(50)$ refers to the particle size below which 50% of the volume of material exists; and $Dv(90)$ refers to the particle size below which 90% of the volume of material exists.

Other Routes of Delivery.

Other routes of delivery may be used for administering effective amounts of the progesterone compounds or compositions containing therapeutically effective concentrations of the compounds. For instance, the present invention also contemplates formulations for systemic delivery, including for instance parenteral, oral, or intravenous delivery, or for local or topical application, for the treatment of glucocorticoid-insensitivity related diseases or disorders, or conditions, including, but not limited to, glucocorticoid resistant conditions (e.g., glucocorticoid resistant asthma, refractory rheumatoid arthritis, refractory inflammatory bowel disease, chronic obstructive pulmonary disease and acute respiratory distress syndrome, interstitial pulmonary fibrosis, and cystic fibrosis); glucocorticoid refractory conditions (e.g., refractory ulcerative colitis, children with severe Crohn disease, corticosteroid refractory asthma, desquamative interstitial pneumonia refractory to corticosteroid, refractory inflammatory myopathies, refractory myasthenia gravis, refractory pemphigus vulgaris, methotrexate-refractory RA patients, refractory nephrotic syndrome, refractory multiple sclerosis, refractory sprue-like disease, steroid-resistant sarcoidosis, refractory mucosal lesions of pemphigus vulgaris, refractory Schnitzler syndrome, resistant dermatitis of the head and neck, severe refractory atopic dermatitis, refractory Idiopathic thrombocytopenia purpura, refractory orbital myositis, refractory or recurrent lymphomas, critically ill patients with sepsis or acute respiratory distress syndrome (ARDS) and relative adrenal insufficiency); glucocorticoid dependent conditions (e.g., rosacea, polymyalgia rheumatic, giant cell arteritis, polymyositis, dermatomyositis, Kawasaki syndrome, Guillain-Barre syndrome, chronic inflammatory demyelinating polyneuropathy, multifocal motor neuropathy, Stiff man syndrome, corticosteroid dependent systemic lupus erythematosus, corticosteroid dependent multiple sclerosis, symptomatic corticosteroid dependent asthma, primary Sjogren's syndrome, systemic vasculitis, polymyositis, organ transplants, and graft-versus-host disease); and other inflammatory diseases, autoimmune diseases, hyperproliferative diseases, and other such disease when glucocorticoid-insensitivity is implicated. Exemplary of these diseases are lupus, osteoarthritis, rhinosinusitis, polyarteritis nodosa, Wegener's granulomatosis, giant cell arteritis, allergic rhinitis, urticaria, hereditary angioedema, tendonitis, bursitis, autoimmune chronic active hepatitis, cirrhosis, transplant rejection, psoriasis, dermatitis, malignancies (e.g., leukemia, myelomas, lymphomas), acute adrenal insufficiency, rheumatic fever, granulomatous disease, immune proliferation/apotosis, hypothalamic-pituitary-adrenal (HPA) axis suppression and regulation, hypercortisolemia, modulation of the Th1/Th2 cytokine balance, chronic kidney disease, spinal cord injury, cerebral edema, thrombocytopenia, Little's syndrome, Addison's disease, autoimmune hemolytic anemia, uveitis, pemphigus vulgaris, nasal polyps, sepsis, infections (e.g., bacterial, viral, rickettsial, parasitic), type II diabetes, obesity, metabolic syndrome, depression, schizophrenia, mood disorders, Cushing's syndrome, anxiety, sleep disorders, memory and learning enhancement, or glucocorticoid-induced glaucoma, atopic dermatitis, drug hypersensitivity reactions, serum sickness, bullous dermatitis herpetiformis, contact dermatitis, exfoliative erythroderma, mycosis fungoides, pemphigus, nonsuppurative thyroiditis, sympathetic ophthalmia, uveitis and ocular inflammatory conditions unresponsive to topical steroids, allergic bronchopulmonary aspergillosis, fulminating or disseminated pulmonary tuberculosis when used concurrently with appropriate chemotherapy, hypersensitivity pneumonitis, idiopathic bronchiolitis obliterans with organizing pneumonia, idiopathic eosinophilic pneumonias, idiopathic pulmonary fibrosis, *Pneumocystis carinii* pneumonia (PCP) associated with hypoxemia occurring in an HIV(+) individual who is also under treatment with appropriate anti-PCP antibiotics, a diuresis or remission of proteinuria in nephritic syndrome, without uremia, of the idiopathic type or that due to lupus erythematosus, ankylosing spondylitis, polymyalgia rheumatic, psoriatic arthritis, relapsing polychondritis, trichinosis with neurologic or myocardial involvement, and tuberculous meningitis.

Generally, in accordance with the present invention, the methods described herein for the treatment of glucocorticoid-insensitivity related diseases or disorders, or conditions comprise administering a pharmaceutical composition comprising a steroid hormone. Typically, the lipophilic gonadal steroid hormone is a progestogen. The progestogen may be a naturally occurring progestogen or a synthetic progestogen (i.e., a progestin). Progestogens that can be used in accordance with the present invention are grouped into the following categories: progesterone, retroprogesterone, progesterone derivative, 17-OHPC progesterone derivatives (both pregnanes and norpregnanes), 19-norprogesterone derivatives, 19-nortestosterone derivatives (both estranges and gonanes), and spironolactone derivatives. Generally, the progestogen for use in accordance with the present invention is selected from the group consisting of progesterons and their derivatives or active metabolites. Specific examples of progestogens that may be used in the methods and kits of the present invention include, but are not limited to, 17-OHPC, natural progesterone, dydrogesterone, medrogestone, medroxyprogesterone, megestrol acetate, chlormadinone acetate, cyproterone acetate, gestonorone caproate, nomegestrol acetate, demegestone, promegestone, nestorone, trimegestone, norethisterone acetate, norethisterone, lynestrenol, ethynodiol diacetate, norgestrel, levonorgestrel, desogestrel, etonogestrel (3-ketodesogestrel), gestodene, norgestimate, noreigestromin (17-deacetyl norgestimate), dienogest, drospirenone, norethynodrel, 19-nortestosterone, dienogest, cyproterone acetate, tibolone, 19-norprogesterone, and drospirenone.

Other agents that can be used in accordance with the methods and kits of the present invention include, for example, any pharmaceutically-acceptable progestogen derivatives, i.e., derivatives of 17-OHPC, natural progesterone, dydrogesterone, medrogestone, medroxyprogesterone, megestrol, chlormadinone, cyproterone, gestonorone caproate, nomegestrol acetate, demegestone, promegestone, nestorone, trimegestone, norethisterone, norethisterone, lynestrenol, ethynodiol diacetate, norgestrel, levonorgestrel, desogestrel, etonogestrel (3-ketodesogestrel), gestodene, norgestimate, noreigestromin (17-deacetyl norgestimate), dienogest, drospirenone, norethynodrel, 19-nortestosterone, dienogest, cyproterone, tibolone, norprogesterone, and drospirenone. Each progestogen can be derivatized as the corresponding salts, esters, enol ethers or esters, acids, bases, solvates, hydrates or prodrugs prior to formulation, as described herein. Representative pharmaceutically-acceptable salts include, but are not limited to, amine salts, such as but not limited to, chloroprocaine, choline, ammonia; diethanolamine and other hydroxyalkylamines, ethylenediamine, Nmethylglucamine, procaine, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc, aluminum, and other metal salts, such as but not limited to sodium hydrogen phosphate and disodium phosphate; and also including, but not limited to, salts of mineral adds, such as but not limited to hydrochlorides and sulfates; and salts of organic adds, such as but not limited to acetates, lactates, malates, tartrates, citrates, ascorbates, succinates, butyrates, valerates and fumarates. For example, the organic add of acetates is often used such as megestrol acetate, chlormadinone acetate, cyproterone acetate, gestonorone caproate, nomegestrol acetate, and cyproterone acetate.

Additional representative agents that can be used in accordance with the methods and kits of the present invention include, for example, any progestogen active metabolite including, but not limited to, active metabolites of 17-OHPC, natural progesterone, dydrogesterone, medrogestone, medroxyprogesterone, megestrol acetate, chlormadinone acetate, cyproterone acetate, gestonorone caproate, nomegestrol acetate, demegestone, promegestone, nestorone, trimegestone, norethisterone acetate, norethisterone, lynestrenol, ethynodiol diacetate, norgestrel, levonorgestrel, desogestrel, etonogestrel (3-ketodesogestrel), gestodene, norgestimate, norelgestromin (17-deacetyl norgestimate), dienogest, drospirenone, norethynodrel, 19-nortestosterone, cyproterone acetate, tibolone, 19-norprogesterone, and drospirenone. For example, active metabolites of progesterone include allopregnanolone and 5alphapregnan-3,20-dione the active metabolite, Active metabolites of 17-OHPC include M13 monohydroxy-; M12, monohydroxy-; M19, monohydroxy-; M7, dihydroxy-; and M16, monohydroxy-.

In various embodiments, another group of steroid hormone, glucocorticoids, for use in accordance with the present invention is preferably selected from the group consisting of naturally produced steroid hormones, or synthetic compounds, that inhibit the process of inflammation. Specific examples of glucocorticoids include, but are not limited to, hydrocortisone (cortisol), cortisone acetate, dexamethasone (hereinafter, "Dexamethasone"), prednisone, prednisolone, methylprednisolone, betamethasone, triamcinolone, beclometasone, Paramethasone, fluticasone, fludrocortisone acetate, deoxycorticosterone acetate (DOCA), Fluprednisolone, fluticasone propionate, budesonide, beclomethasone dipropionate, flunisolide and triamcinolone acetonide.

In practicing the methods of the present invention, effective amounts of the compounds or compositions containing therapeutically effective concentrations of the compounds, are preferably formulated for systemic delivery, including parenteral, oral, or intravenous delivery, or for local or topical application. For example, the pharmaceutical composition may be administered by subcutaneous, intravenous, intraperitoneal, intraarterial or intramuscular injection; rectally; by transdermally delivery; intravaginal delivery; or buccally; or by oral delivery. When administered by subcutaneous or intramuscular injection, the steroid hormone is suitably formulated as a depot formulation to allow for sustained release of the steroid hormone over an extended period of time. When administered by topical administration, including intravaginal delivery, delivery may suitably be, for example, via a solution, suspension, emulsions or the like and are preferably formulated as creams, gels, ointments, emulsions, solutions, elixirs, lotions, suspensions, tinctures, pastes, foams, aerosols, irrigations, sprays, suppositories, bandages, dermal patches or any other formulations suitable for the route.

With respect to the frequency of administration, any frequency which achieves the desired result (i.e., steroid-sparing in corticosteroid-dependent patients, better responsiveness or tolerance to corticosteroids, achieving efficacy by using a lower dose of corticosteroid, preventing individuals at risk for developing refractory responses or resistance or exacerbations in response to antigen exposures, infections, exercise, or irritants, achieving optimal immune-functions, easier responses for the subject when steroid administration is tapered or withdrawn, or after prolonged administration of corticosteroids, decreased risks for developing corticosteroid-related adverse events such as opportunistic infections and bone loss, and combinations thereof, may be used. The frequency of administration will preferably be determined, at least in part, by the steroid hormone(s) and/or dosage form selected. In various embodiments, the pharmaceutical composition is preferably administered at an interval exceeding daily or once per week. For example, the pharmaceutical composition may be administered once every other week, once monthly, once every two months, or once every three months. In various other embodiments, the pharmaceutical composition is administered once weekly, or at an interval of less than one week (e.g., daily or every other day). For example, when the steroid hormone is 17-OHPC, administration may suitably be via daily, once-weekly or once every two-week, or once-monthly or once every 3-month injections. Those ordinary skill in the art will understand that the route of administration and frequency of administration for the pharmaceutical compositions used in the methods and kits of the present invention will depend on a variety of factors including, for example, the particular steroid hormone(s) used, the formulation in which it is delivered, the tissue being treated, the age and gender of the individual treated, in vivo or in vitro test data, and the professional judgment of the particular patient's needs. The dosing frequency ranges set forth herein are exemplary only and are not intended to limit the scope or practice of formulations provided herein.

A person of ordinary skill in the art will also appreciate that appropriate dosing of the steroid hormone will depend on the steroid hormone(s) selected, the route of administration and dosage form, the frequency of administration, the disease(s) to be treated, the metabolic stability and length of action of that compound, the species, age, body weight, general health, and diet of the subject, rate of excretion, drug combination, and severity of the particular condition. The effective amount of a steroid hormone provided herein can be determined by one of ordinary skill in the art, and includes exemplary dosage amounts for a mammal of from about 0.001 to 100 mg/kg of body weight of active compound given orally per day. For example, to achieve the endometrium and antigonadotropic effects (i.e., dose for ovulation inhibition) 0.15 mg/day p.o. for levonorgestrel or desogestrel is preferably desired while the required amount is much higher, 5-10 mg/day for medroxyprogesterone acetate or 200-300 mg/day for progesterone.

A preferably desired dose of budesonide for the treatment of asthma may be one to four inhalations of 90 μg to 400 μg once or twice daily. Another preferred budesonide dose may be between 0.25 mg to 1 mg total daily dose given once or twice daily in divided doses. A much lower or higher dose of budesonide may be selected when formulated and administered in combination with a progestogen, such as 17-OHPC. The dosing ranges set forth herein are exemplary only and are not intended to limit the scope or practice of formulations provided herein.

A preferably desired dose of fluticasone for the treatment of asthma may be one to four inhalations of 50 μg to 500 μg, and up to 2000 μg, once or twice daily. Another preferred fluticasone dose may be up to 880 μg given once or twice daily to patients that have previously been treated with corticosteroids. Another preferred fluticasone dose may be between 100 μg to 500 μg given once or twice daily to patients that have previously been treated with bronchiodilators. Another preferred fluticasone dose may be up to 1000 μg given once or twice daily to patients that have previously been treated with oral corticosteroids. Another preferred fluticasone dose may be between 50 μg to 1000 μg given once or twice daily to pediatric patients. Pediatric dosages may vary dependent on a patient's health history and previous treatment with bronchiodilators, inhaled corticosteroids, and/or oral corticosteroids. A much lower or higher dose of fluticasone may be selected when formulated and administered in combination with a progestogen, such as 17-OHPC. The dosing ranges set forth herein are exemplary only and are not intended to limit the scope or practice of formulations provided herein.

A person of ordinary skill in the art will also appreciate that appropriate dosing of the steroid hormone depends on gender as progestogen is a sex hormone. Progesterone is primarily secreted by the granulosa cells and the corpus luteum in the ovary. During pregnancy, a major source of progesterone also comes from the placenta. Males produce progesterone in the adrenal gland and testes, as this is a precursor of testosterone. In women, progesterone levels are relatively low during the preovulatory phase of the menstrual cycle, rise after ovulation, and are elevated during the luteal phase. Progesterone levels tend to be <2 ng/ml prior to ovulation, and >5 ng/ml after ovulation. If pregnancy occurs, progesterone levels are initially maintained at luteal levels, With the onset of the luteal-placental shift in progesterone support of the pregnancy, levels start to rise further and may reach 100-200 ng/ml at team. The reference range for progesterone levels in adult men is 0.13-097 ng/ml. Adult males have levels similar to those in women during the follicular phase of the menstrual cycle as well as the level in postmenopausal women. Clearly, women regularly experience a 17-fold change in serum progesterone concentration during the menstrual cycle, or more than 100-fold increase in pregnancy. Thus, tolerance or maximum dose or minimal effective dose of progestogen treatment would be higher in women than in males. For example, when the steroid hormone is 17-OHPC and a common dosage used is 150-500 mg weekly injection for its uses in women-health related indications, Given some important effects of progesterone on restoring corticosteroid sensitivity are assumed to be mediated non-genomically through different molecular biological modes of action (i.e., functions not related to progestational activity), this may result in some pharmacodynamic variability. A much lower or higher dose of progestogen (e.g. 17-OHPC) may be selected as well as a different dosage level for male subjects. The dosing ranges set forth herein are exemplary only and are not intended to limit the scope or practice of formulations provided herein.

Exemplary Dosage Forms and Dosage Administrations.

Preferably, the pharmaceutical compositions of the present invention contain: i) a physiologically acceptable carrier, diluent, or excipient, or a combination thereof; and ii) one or more steroid hormone(s) as described herein. The compositions can be formulated for single dosage administration or for multiple dosages. Dosage forms or compositions containing steroid hormone(s), for instance, in the range of about 0.005% to about 100%, with the balance of the dosage form or composition made up of one or more non-toxic carriers and/or pharmaceutically acceptable excipients, can be prepared.

For example, an exemplary pharmaceutical composition in accordance with the present invention may contain one or more diluents, one or more carriers, one or more binders, one or more coatings, one or more lubricants, one or more solvents, one or more buffers, one or more preservatives, one or more flavoring agents, one or more dyes, and/or one or more absorption enhancers, and/or one or more biodegradable polymers.

The particular excipient(s) included in the pharmaceutical composition will depend on the particular steroid hormone(s) and dosage form selected, and the skilled artisan will be able to readily select appropriate excipients once the steroid hormone(s) and the dosage form therefore have been chosen.

For example, for oral administration, a pharmaceutically acceptable non-toxic composition in accordance with the present invention can preferably be formed by the incorporation of any of one or more normally employed excipients, such as, for example, pharmaceutical grades of mannitol, lactose, Respitose ML001, Lactohale LH300, starch, magnesium stearate, talcum, cellulose derivatives, sodium croscarmellose, glucose, sucrose, magnesium carbonate or sodium saccharin. Such compositions preferably include, for instance, solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others.

Another example of a pharmaceutically acceptable non-toxic composition in accordance with the present invention, includes an injectable formulation. An injectable formulation can be prepared in conventional forms, for instance, either as liquid solutions or suspensions, solid forms suitable for solution or suspension in liquid prior to injection, or as an emulsion. Suitable excipients include, for example, water, saline, dextrose, glycerol, mannitol, 1,3-butanediol, Ringer's solution, an isotonic sodium chloride solution or ethanol. According to another example, an injectable suspension can be prepared using one or more appropriate liquid carriers, suspending agents and the like. Certain pharmaceutical compositions for injection can be presented in unit dosage form, e.g., in ampules or in multi dose containers. Certain pharmaceutical compositions for injection include, for example, suspensions, solutions or emulsions in oily or aqueous vehicles, and may contain one are more pharmaceutically acceptable excipient agents such as, for instance, one or more suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes.

In addition to administration of a progestogen hormone, the formulations (e.g., inhalation formulations) and methods of the present invention may further comprise administration of one or more additional therapeutic agents aimed at the treatment of glucocorticoid insensitivity related diseases or disorders, or conditions, as discussed herein. Examples of additional therapeutic agents include, for example, glucocorticoid (e.g., hydrocortisone, cortisone acetate, dexamethasone, prednisone, prednisolone, methylprednisolone, betamethasone, triamcinolone, beclometasone, Paramethasone, fluticasone, fludrocortisone acetate, deoxycorticosterone acetate, Fluprednisolone, fluticasone propionate, budesonide, beclomethasone dipropionate, flunisolide and triamcinolone acetonide, an androgen (e.g., dehydroepiandrosterone (DHEA)), an estrogen (e.g., estradiol), immunosuppressive or immunomodulators agents (e.g., cyclosporine, methotrexate, gold, 6-mercaptopurine, biologic products such as etanercept, and adalimumab, intravenous immunoglobulin and Mepolizumab), and calcineurin inhibitors (e.g., cyclosporin, tacrolimus), p38 MAP kinase inhibitors, JNK inhibitors (decrease API), Vitamin D, MIF inhibitors, Histone deacetylate-2 activators, Theophylline, Phosphoinositide-3-kinase-δ inhibitors, leukotriene modifiers, long-acting beta agonists, antioxidants, iNOS inhibitors, muscarinic receptor antagonist, bronchodilators, anticholinergic agents, narrow spectrum kinase inhibitors, and P-glycoprotein inhibitors, and combinations thereof.

The other therapeutic agents, when employed in combination with the agents described herein, can be used, for example, in those amounts indicated in the Physicians' Desk Reference (PDR) or as otherwise determined by one of ordinary skill in the art. The amount of an agent used with non-oral routes is preferably determined based upon corresponding serum concentration level of an oral dosage or containing a quantity of the active compound in an amount sufficient to alleviate the symptoms of the treated subject. In the formulations and methods provided herein, such other pharmaceutical agent(s) can be administered prior to, simultaneously with, or following the administration of the compounds provided herein.

Therapeutic effects of the use of a glucocorticoid sensitizer include any, but not limited to, dosing-sparing of concurrent treatment drugs above, better responsive or tolerant to concurrent treatment drugs, achieving efficacy by using lower dose of concurrent treatment drugs, preventing individuals at risk for developing refractory responses or resistance of concurrent treatment drugs, achieving optimal immune-functions, easier responses after tapering or withdrawal of concurrent treatment drugs, or prolonged administration of concurrent treatment drugs, decreased risks for developing drug-related adverse events due to concurrent treatment drugs, and combinations thereof.

Increasing HPH Cycles Reduces 17-0HPC Size

Figure 3:
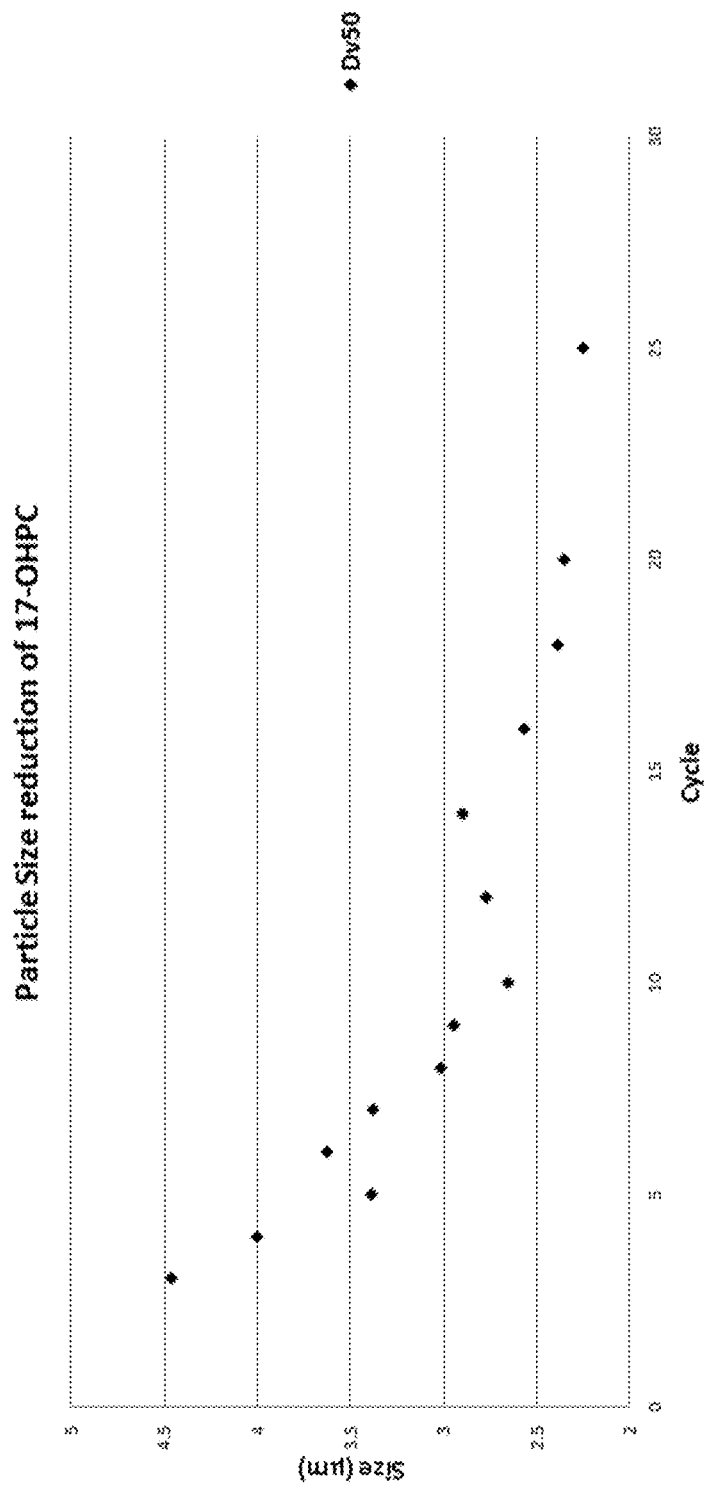
FIG. 3 is a graphical representation of Dv50 particle size distribution values of 17-OHPC after milling in water and after spray drying.

In a preferred embodiment of the invention, size reduction on 17-OHPC was performed via HPH. In the preferred embodiment of the invention, the suspension of 17-OHPC using water as an anti-solvent was prepared at approximately 5% w/w and 15% of the total mass of solids of Tween-80 was milled at a pressure of 1400 bar (hydraulic pressure at 90 bar). Particle size distributions were measured using a Malvern Mastersizer 2000S. The particle size distribution profile for each HPH cycle is shown in FIG. 1. Particle sizes are listed in FIG. 2 and are expressed as Dv10, Dv50, Dv90, and span wherein Dv10 refers to the particle size below which 10% of the volume of material exists; Dv50 refers to the particle size below which 50% of the volume of material exists; and Dv90 refers to the particle size below which 90% of the volume of material exists. These exemplary results demonstrate that there is a decrease of particle size with increasing cycle number from the bulk material to cycle five (Dv50=3.393 μm), with a first unexpected increase in Dv50 particle size at cycle six (3.634 μm). See FIG. 3. Dv50 particle size appears to reach a first asymptote between cycle eight to ten (with a Dv50 range between 3.021 μm and 2.664 μm, respectively). After this first intermediate particle size range, there is a second unexpected increase in particle size from cycle 10 to cycle 12 (2.664 μm to 2.781 μm). A second intermediate Dv50 particle size reduction was then observed where the Dv50 values asymptote toward another particle size with range from cycle 12 to cycle 20 (2.78 μm to 2.3 μm, respectively). The Dv50 also levels at ~2.3 μm at cycle 18 and cycle 20.

Surprisingly, an additional size reduction is further achieved after cycle 25, wherein Dv50 particle size further reduces to 2.255 μm.

Size Reduction and Spray-Drying.

Spray drying is a method of rapidly drying a liquid slurry to a dry powder using gas. A liquid stream such as a solution, suspension, or emulsion of an API is sprayed into a chamber in the presence of hot gas. During the process the drug is dried and atomized, and is then separated from the drying gas by a cyclone or bag-filter. Gil. M. et al. Chem. Today 2010. 28(4)18-22.

Combination spray drying such as the H42 process combines spray drying with high pressure homogenization. In the H42 process, a drug is spray dried following the synthesis of a drug. The spray dried drug product is then passed through high pressure homogenization for further size reduction. Keck C., et al., Dosis 2008. 24(2)124-128.

17-OHPC particle size reduction was achieved by HPH in water (2.5% w/w) without the presence of surfactant Tween-80. After particle size reduction, the particles were recovered from the suspension using a spray-drying process. Spray drying was used to optimize the wet milling process of particle size reduction; i.e., particle size reduction was achieved by HPH followed by spray drying. This approach enabled the crystalline structure of the particles to be maintained without the formation of significant levels of amorphous material.

Figure 4:
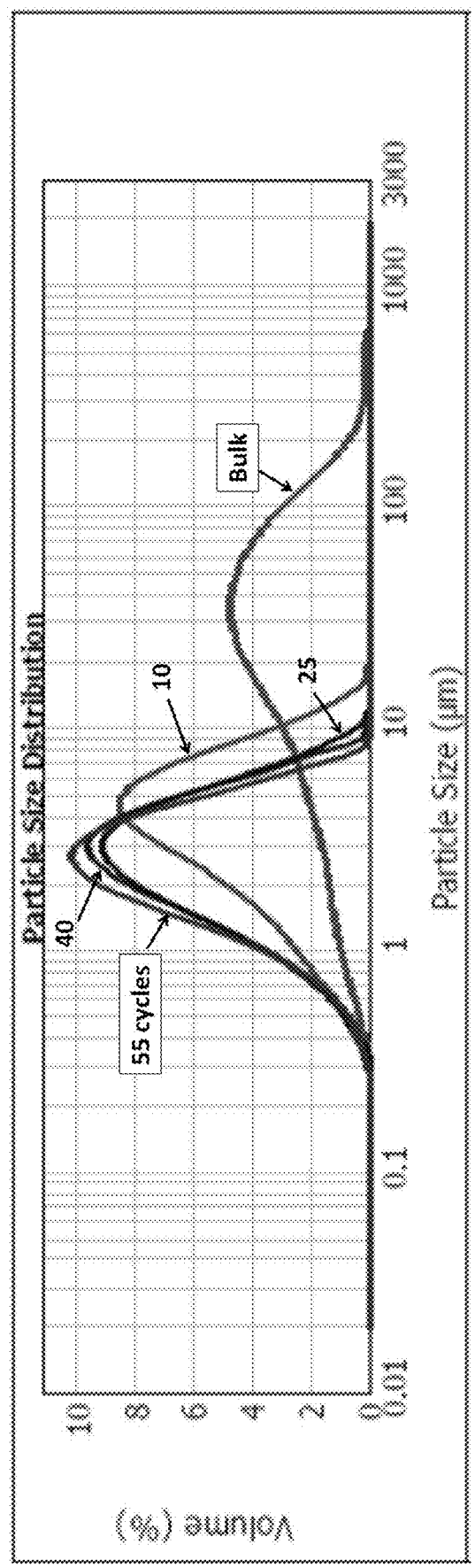
FIG. 4 is an exemplary comparison of particle size distribution profiles of 17-OHPC powder obtained after HPH in water and after spray drying.
Figure 6:
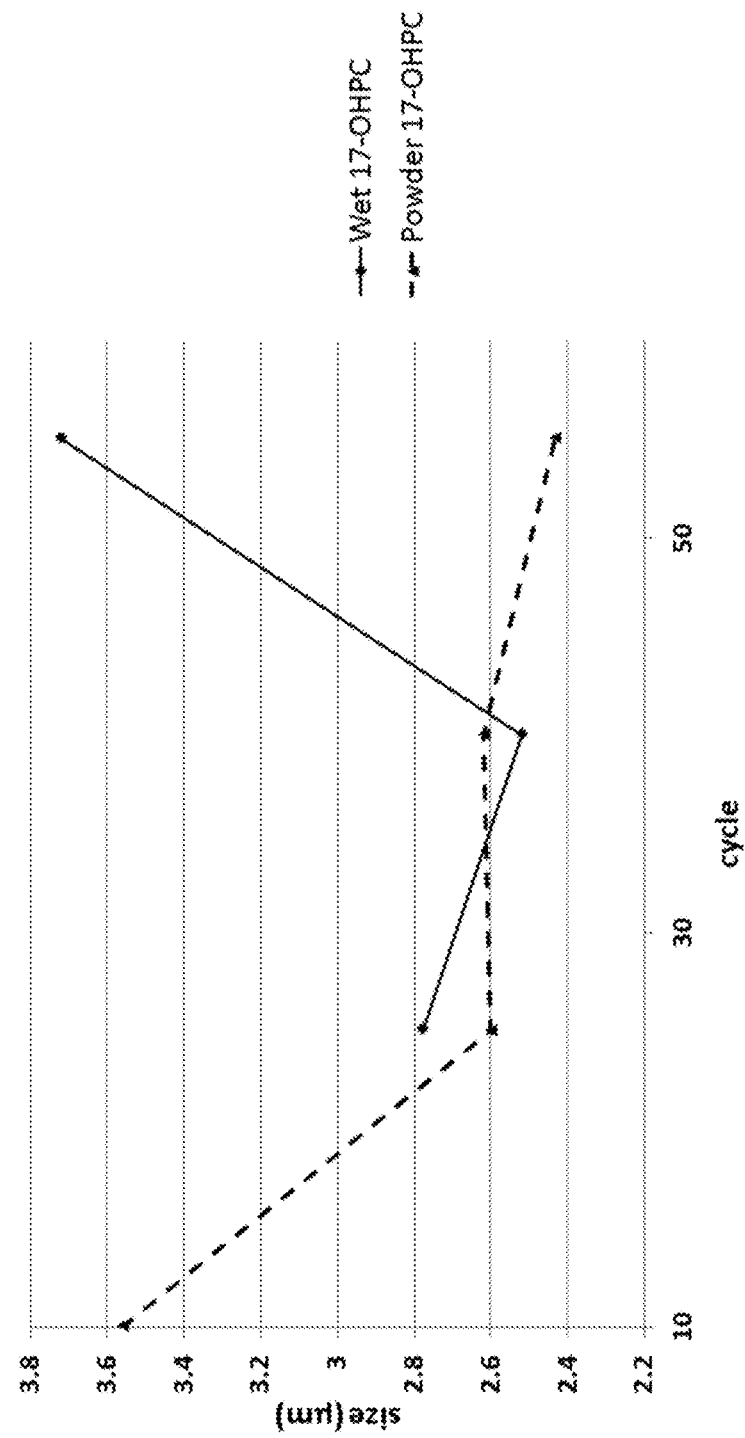
FIG. 6 is a graphical representation of the FIG. 5 results.

API particle size distribution after HPH was compared between 17-OHPC in water before (wet) and after spray drying (powder). Particle size reduction was achieved by HPH in water (2.5% w/w) without surfactant Tween-20. The particle size distribution profile for 17-OHPC after HPH in water is shown in FIG. 4. Particle sizes distribution values for wet and powder 17-OHPC are listed in FIG. 5 and expressed as Dv10, Dv50, and Dv90, and span, wherein Dv10 refers to the particle size below which 10% of the volume of material exists; Dv50 refers to the particle size below which 50% of the volume of material exists; and Dv90 refers to the particle size below which 90% of the volume of material exists. The particle size of wet 17-OHPC after 55 HPH cycles was higher than after 40 HPH cycles due to agglomeration. After particle size reduction, the particles were recovered from the suspension using a spray-drying process. Spray drying was used to optimize the wet milling process of particle size reduction; i.e., particle size reduction was achieved by HPH followed by spray drying. The spray drying process following HPH further reduced the size of 17-OHPC, in particular, 17-OHPC after 55 cycles. FIG. 6 compares the wet and powder 17-OHPC Dv50 size distribution and shows that there was a further size reduction of particle size after spray drying.

Figure 7:
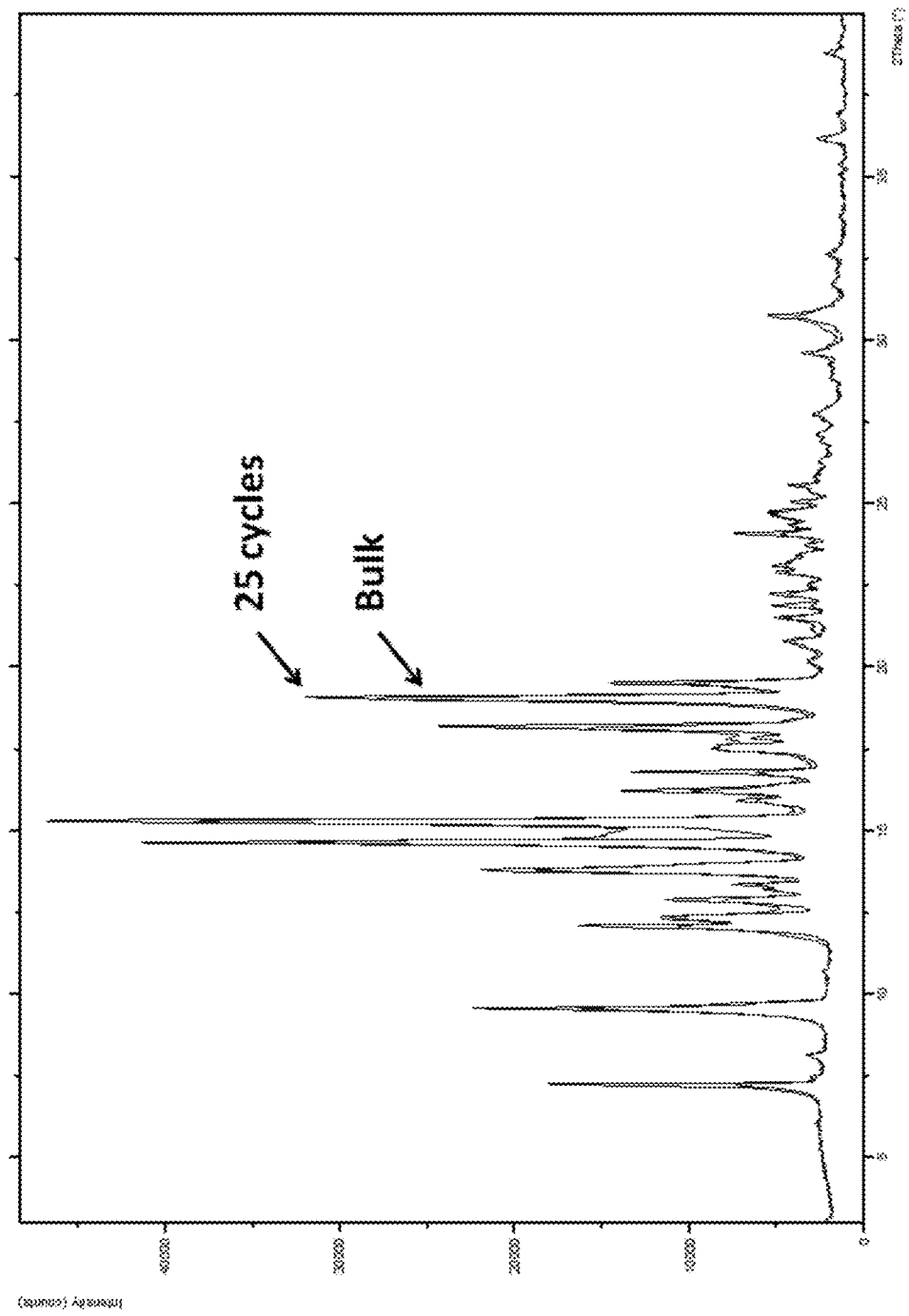
FIG. 7 is an exemplary comparison of XPRD profiles between bulk material and 17-OHPC powder after spray drying.

The powder obtained after spray drying 17-OHPC processed through 25 HPH cycles was analyzed by XRPD. The obtained spray dried powder and the pre-spray dried 17-OHPC had similar XRPD profiles, signifying that the spray drying process did not change the crystalline structure of 17-OHPC. See FIG. 7. Thus, this approach provides suitable control over the particle size distribution and enables maintenance of crystalline structure, without the formation of significant levels of amorphous material.

Figure 8:
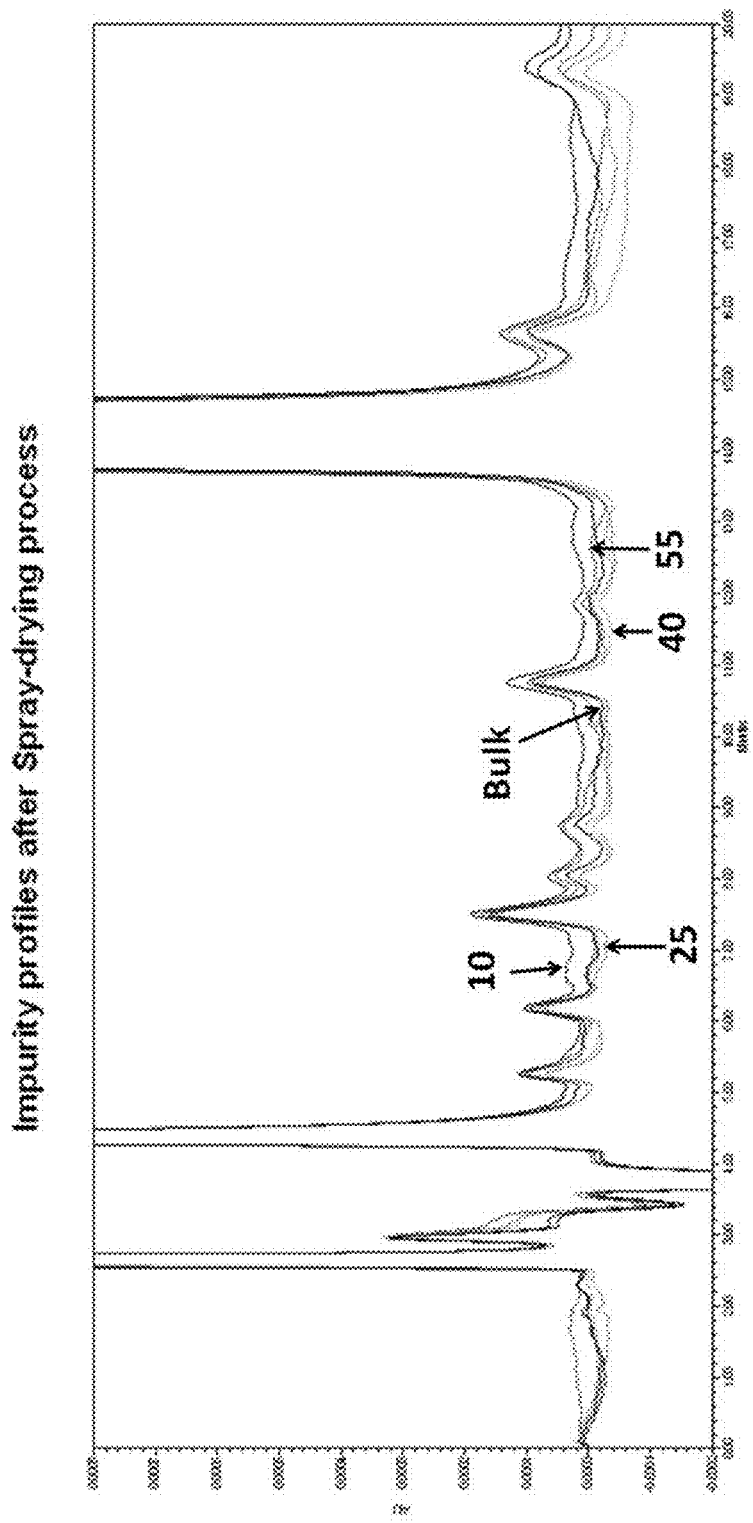
FIG. 8 is an exemplary High Pressure Liquid Chromatography (HPLC) data showing the impurity profile of bulk and spray dried 17-OHPC.

Referring to FIG. 8, another exemplary powder blend formulation of 17-OHPC demonstrates that the obtained powders after spray drying have similar impurity profiles when compared to the formulated material prior to spray drying as analyzed by High Pressure Liquid Chromatography (HPLC). Impurities of 17-OHPC after 10, 25, 40, and 55 HPH cycles and after spray drying were similar to those of the bulk material, FIG. 9. The resultant powders and the bulk material have similar area percentage of impurities, meaning that the HPH and spray drying process does not generate any extra impurities.

While the specification describes particular embodiments of the present invention, those of ordinary skill in the art can devise variations of the present invention without departing from the inventive concept.

We claim:

1. A method of preparing a composition comprising 17alpha-hydroxyprogesterone caproate, said method comprising:
   (a) preparing a bulk material of a pharmaceutical formulation powder comprising 17-alphahydroxyprogesterone caproate, wherein the bulk material is prepared for milling in water using a number of cycles;
   (b) milling the bulk material using at least 25 cycles and no more than 55 cycles in water to reduce the bulk material to a fine particulate, wherein the fine particulate has a Dv50 particle size that is 278 µm after cycle 25 and 2.521 µm after cycle 40 and a span distribution value of 1.636 after 25 cycles and 1.505 after 40 cycles; wherein the milling is performed in the absence of a surfactant;
   (c) recovering the fine particulate by spray-drying; and
   (d) blending the fine particulate with lactose monohydrate to generate the composition, wherein the lactose monohydrate comprises 90% or 99% by weight in the composition.

2. The method of claim 1, wherein said pharmaceutical formulation powder comprises a glucocorticoid.

3. A method of preparing a composition comprising 17alpha-hydroxyprogesterone caproate, said method comprising the following steps:
   a) preparing a bulk material of a pharmaceutical formulation powder comprising 17-alphahydroxyprogesterone caproate;
   b) milling the bulk material in water using a number of cycles to reduce the bulk material to a fine particulate, wherein the fine particulate has a Dv50 particle size that is 2.78 µm after cycle 25 and 2.521 µm after cycle 40, and wherein the fine particulate has a span distribution value of 1.636 after 25 cycles and 1.505 after 40 cycles, wherein the number of cycles after cycle 55 results in agglomeration of the fine particulates; and
   c) spray drying the fine particulate;
   wherein the milling is performed in the absence of a surfactant.

4. The method of claim 3, wherein said bulk material further comprises an excipient suitable for inhalation.

5. The method of claim 3, wherein said pharmaceutical formulation powder further comprises a glucocorticoid.

6. The method of claim 5, wherein said glucocorticoid is budesonide or fluticasone.

7. The method of claim 4, wherein the excipient suitable for inhalation comprises 90% by weight of lactose monohydrate.

8. The method of claim 4, wherein the excipient suitable for inhalation comprises 99% by weight of lactose monohydrate.

* * * * *

UNITED STATES PATENT AND TRADEMARK OFFICE
CERTIFICATE OF CORRECTION

| | | |
|---|---|---|
| PATENT NO. | : 10,993,879 B2 | Page 1 of 1 |
| APPLICATION NO. | : 14/860578 | |
| DATED | : May 4, 2021 | |
| INVENTOR(S) | : Chang Lee and Tao Tom Du | |

It is certified that error appears in the above-identified patent and that said Letters Patent is hereby corrected as shown below:

On the Title Page

Please change item (71) Applicant and item (73) Assignee name from:
"SHENZHEN EVERGREEN HERAPEUTICS CO., LTD., Shenzhen, CHINA"
To:
"SHENZHEN EVERGREEN THERAPEUTICS CO., LTD., Shenzhen, CHINA"

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*